United States Patent
Sanders et al.

(10) Patent No.: US 6,417,223 B1
(45) Date of Patent: Jul. 9, 2002

(54) TOCOPHEROLS, TOCOTRIENOLS, OTHER CHROMAN AND SIDE CHAIN DERIVATIVES AND USES THEROF

(75) Inventors: Bob G. Sanders; Kimberly Kline; Laurence Hurley; Robb Gardner; Marla Menchaca; Weiping Yu; Puthucode N. Ramanan; Shenquan Liu; Karen Israel, all of Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/404,001

(22) Filed: Sep. 23, 1999

Related U.S. Application Data

(60) Provisional application No. 60/101,542, filed on Sep. 23, 1998, now abandoned.

(51) Int. Cl.$^7$ ............................................... A01N 43/16
(52) U.S. Cl. ..................... 514/456; 514/458; 549/408; 549/410; 549/412
(58) Field of Search ................................ 549/408, 410, 549/412; 514/456, 458

(56) References Cited

U.S. PATENT DOCUMENTS

| | | | | |
|---|---|---|---|---|
| 3,869,477 A | * | 3/1975 | Shindo et al. | 260/345.5 |
| 4,457,918 A | | 7/1984 | Holick et al. | 424/180 |
| 4,645,845 A | * | 2/1987 | Gehrken et al. | 549/407 |
| 4,665,204 A | * | 5/1987 | Wirth | 549/410 |
| 5,114,957 A | | 5/1992 | Hendler | 514/356 |
| 5,135,945 A | | 8/1992 | Robinson et al. | 514/456 |
| 5,260,294 A | * | 11/1993 | Walser | 514/230.5 |
| 5,315,017 A | | 5/1994 | Le Baut et al. | 549/408 |
| 5,393,775 A | * | 2/1995 | Le Baut et al. | 514/456 |
| 5,545,660 A | | 8/1996 | Grisar et al. | 514/458 |
| 5,650,404 A | * | 7/1997 | Ogata et al. | 514/100 |
| 5,917,060 A | * | 6/1999 | Rosenau et al. | 549/408 |
| 5,990,322 A | * | 11/1999 | Lee et al. | 549/410 |
| 6,022,560 A | | 2/2000 | Yazdi et al. | 424/450 |

FOREIGN PATENT DOCUMENTS

| | | | | |
|---|---|---|---|---|
| CS | 172015 | * | 12/1974 | |
| FR | 2672601 | * | 2/1991 | |
| JP | 55-76871 | * | 6/1980 | |
| WO | WO 98/172467 | | 4/1998 | A61K/7/48 |

OTHER PUBLICATIONS

Database CAPLUS on STN (Columbus, OH, USA) No. 93:204461, abstract of JP 55076871 (1980).*
Database CAPLUS on STN (Columbus, OH, USA) No. 89:163408, abstract of cs 172015 (1976).*
Database CAPLUS on STN (Columbus, OH, USA) No. 118:80958, abstract of FR 2672601 (1992).*
Dominguez, X. "Hydroxyacetophenone derivatives from B. glutinosa" J. Nat. Prod. vol. 49, No. 1, pp. 143–144 (1986).*
Fatope, M. et al "Design, synthesis, and testing of potential antisickling agents" J. Med. Chem. vol 30, No. 11, pp. 1973–1977 (1987).*
Fariss, M. et al "The selective antiproliferative of alpha–tocopheryl hemisuccinate . . . " Cancer Res., vol 54, pp. 3346–3351, 1994.*
Caplus abstract of JP 09301969, 1997.*
Caplus abstract of JP 55076871, 1980.*
Database CAPLUS on STN (Columbus, OH, USA) No. 93:204461, abstract of JP 55076871 (1980).*
Database CAPLUS on STN (Columbus, OH, USA) No. 128:82201, abstract of JP 09301969 (1997).*
Welch, S., et al. Syntheses and Activities of Antioxidant Derivatives of Retinoic Acid. *J. Med. Chem*, vol. 25, 1982, pp. 81–84.
Djuric et al. Growth Inhibition of MCF–7 and MCF–10A Human Breast Cells by .Alpha.–Tocopheryl Hemisuccinate Cholesteryl Hemisuccinate and their Ether Analogs. *Cancer Lett*. vol. 111, 1997, pp. 133–139. (abstract).
Farriss et al. The Selective Antiproliferative Effects of α–Tocopheryl Hemisuccinate and Cholesteryl Hemisuccinate on Murine Leukemia Cells Result from the Action of the Intact Compounds. *Cancer Research*. vol. 54, 1994, pp. 3346–3351.

* cited by examiner

Primary Examiner—James O. Wilson
Assistant Examiner—Leigh C. Maier
(74) Attorney, Agent, or Firm—Benjamin Aaron Adler

(57) ABSTRACT

The present invention provides an antiproliferative compound having the structural formula

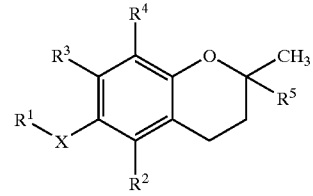

wherein X is oxygen, nitrogen or sulfur; $R^1$ is alkyl, alkenyl, alkynyl, aryl, heteroaryl, carboxylic acid, carboxylate, carboxamide, ester, thioamide, thiolacid, thiolester, saccharide, alkoxy-linked saccharide, amine, sulfonate, sulfate, phosphate, alcohol, ethers and nitriles; $R^2$ is hydrogen, methyl, benzyl carboxylic acid, benzyl carboxylate, benzyl carboxamide, benzylester, saccharide and amine; $R^3$ is selected from the group consisting of hydrogen, methyl, benzyl carboxylic acid, benzyl carboxylate, benzyl carboxamide, benzylester, saccharide and amine; $R^4$ is of methyl, benzyl carboxylic acid, benzyl carboxylate, benzyl carboxamide, benzylester, saccharide and amine; and $R^5$ is alkyl, alkenyl, alkynyl, aryl, heteroaryl, carboxyl, amide and ester. Also provided is a method for inducing apoptosis in a cell comprising administering a composition comprising a compound.

3 Claims, 14 Drawing Sheets

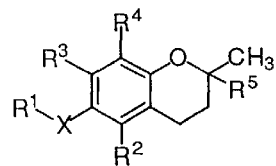

| Compound | $R^1$ | $R^2$ | $R^3$ | $R^4$ | $R^5$ |
|---|---|---|---|---|---|
| 1 | $CH_2CO_2H$ | $CH_3$ | $CH_3$ | $CH_3$ | phytyl |
| 2 | $(CH_2)_2CO_2H$ | $CH_3$ | $CH_3$ | $CH_3$ | phytyl |
| 3 | $(CH_2)_3CO_2H$ | $CH_3$ | $CH_3$ | $CH_3$ | phytyl |
| 4 | $(CH_2)_4CO_2H$ | $CH_3$ | $CH_3$ | $CH_3$ | phytyl |
| 5 | $(CH_2)_5CO_2H$ | $CH_3$ | $CH_3$ | $CH_3$ | phytyl |
| 6 | $(CH_2)_7CO_2H$ | $CH_3$ | $CH_3$ | $CH_3$ | phytyl |
| 7 | $CH_2CO_2H$ | $CH_3$ | H | $CH_3$ | phytyl |
| 8 | $CH_2CO_2H$ | $CH_3$ | H | $CH_3$ | phytyl |
| 9 | $CH_2CO_2H$ | H | H | $CH_3$ | phytyl |
| 10 | $CH_2CONH_2$ | $CH_3$ | $CH_3$ | $CH_3$ | phytyl |
| 11 | $CH_2CO_2CH_3$ | $CH_3$ | $CH_3$ | $CH_3$ | phytyl |
| 12 | $CH_2CON(CH_2CO2H)_2$ | $CH_3$ | $CH_3$ | $CH_3$ | phytyl |
| 13 | $CH_2CH_2OH$ | $CH_3$ | $CH_3$ | $CH_3$ | phytyl |
| 14 | $CH_2CO_2H$ | $CH_3$ | $CH_3$ | $CH_3$ | $CH_3$ |
| 15 | RS $CH_2CO_2H$ | $CH_3$ | $CH_3$ | $CH_3$ | phytyl |

Fig. 2A

| Compound | $R^1$ | $R^2$ | $R^3$ | $R^4$ | $R^5$ |
|---|---|---|---|---|---|
| 16 | $CH_2CO_2H$ | $CH_3$ | $CH_3$ | $CH_3$ | COOH |
| 17 | R/RS $CH_2CO_2H$ | $CH_3$ | $CH_3$ | $CH_3$ | phytyl |
| 18 | $CH_2CO_2H$ | $CH_3$ | $CH_3$ | $CH_3$ | isoprenyl |
| 19 | $NH_3Cl$ | $CH_3$ | $CH_3$ | $CH_3$ | phytyl |
| 20 | $CH_2CO_2H$ | $CH_3$ | $CH_3$ | $CH_3$ | phytyl |
| 21 | $OSO_3NHEt_3$ | $CH_3$ | $CH_3$ | $CH_3$ | phytyl |
| 22 | $CH_2CO_2H$ | $CH_3$ | $CH_3$ | $CH_3$ | phytyl |
| 23 | $CH_2CO_2H$ | $CH_3$ | $CH_3$ | $CH_3$ | phytyl |
| 24 | $CH_2CO_2H$ | $CH_3$ | $CH_3$ | $CH_3$ | phytyl |
| 25 | $CH_2CO_2H$ | $CH_3$ | $CH_3$ | $CH_3$ | phytyl |
| 26 | $CH_2CO_2H$ | $CH_3$ | $CH_3$ | $CH_3$ | other |
| 27 | $CH_2CO_2H$ | $CH_3$ | $CH_3$ | $CH_3$ | other |
| 28 | $CH_2CO_2H$ | $CH_3$ | $CH_3$ | $CH_3$ | ester |
| 29 | $CH_2CO_2H$ | $CH_3$ | $CH_3$ | $CH_3$ | ester |

Phytyl = 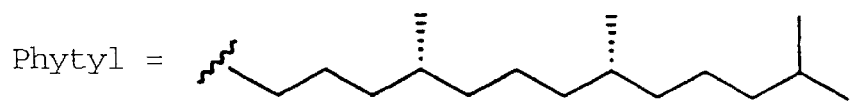

Fig. 2B

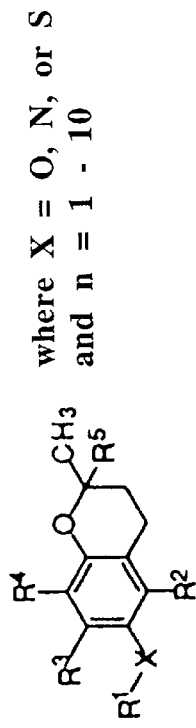
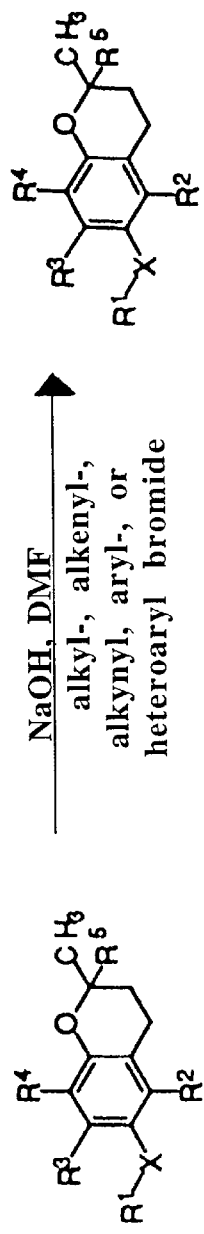
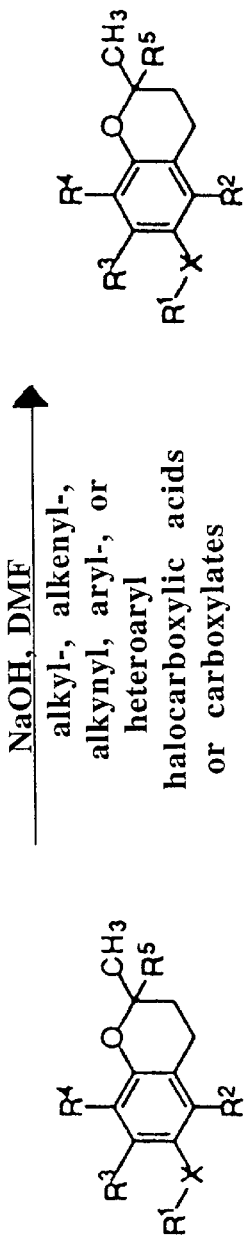

where X = O, N, or S and n = 1 - 10

$R^1$ = alkyl, alkenyl, akynyl, aryl, and heteroaryl.

NaOH, DMF
alkyl-, alkenyl-, alkynyl, aryl-, or heteroaryl bromide $R^1$ = alkyl, alkenyl, akynyl, aryl, and heteroaryl carboxylic acids or carboxylates.

NaOH, DMF
alkyl-, alkenyl-, alkynyl, aryl-, or heteroaryl halocarboxylic acids or carboxylates $R^1$ = alkyl, alkenyl, akynyl, aryl, and heteroaryl carboxylic acids or carboxylates.

Fig. 3A

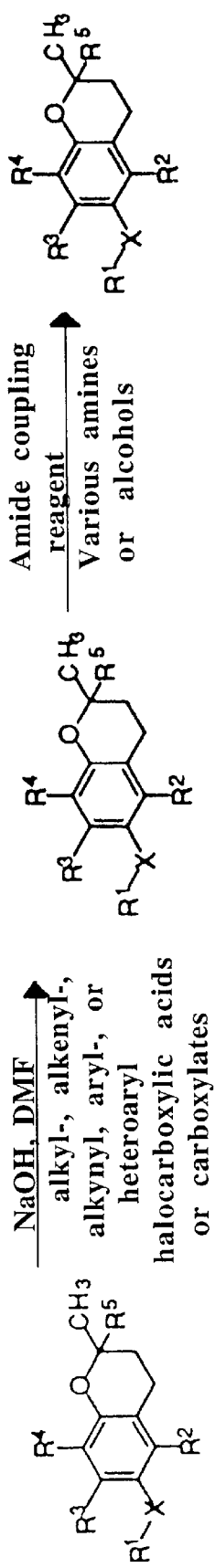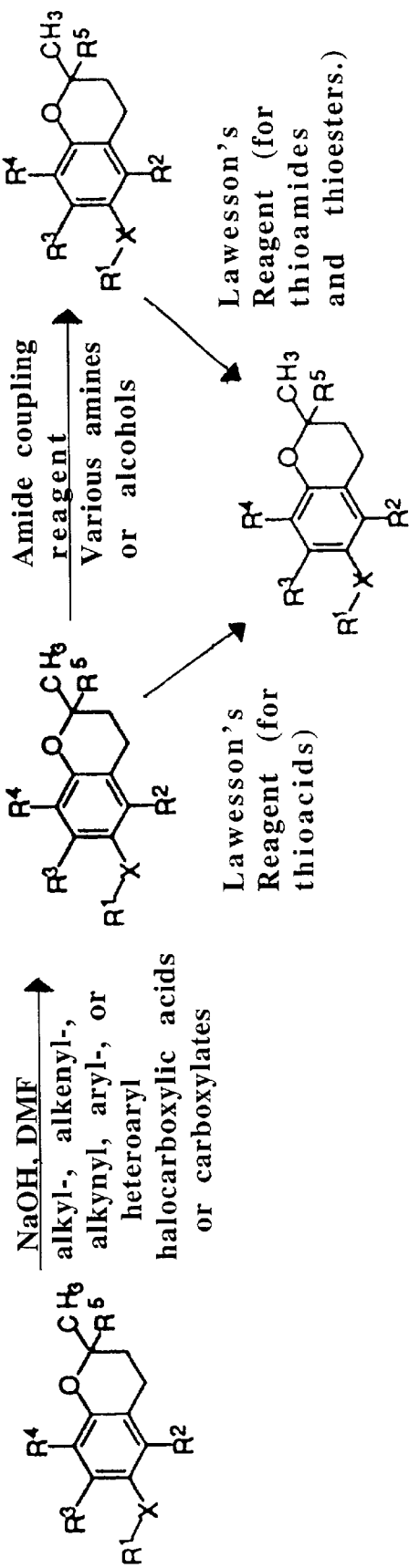
Fig. 3B

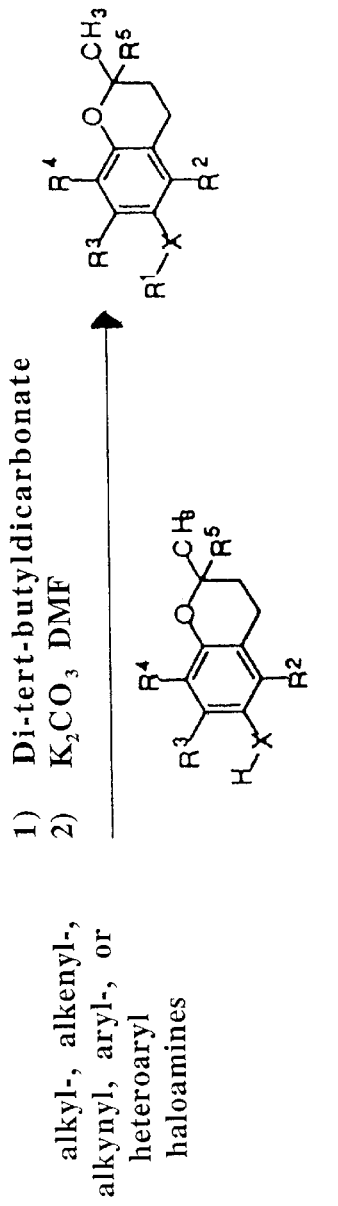
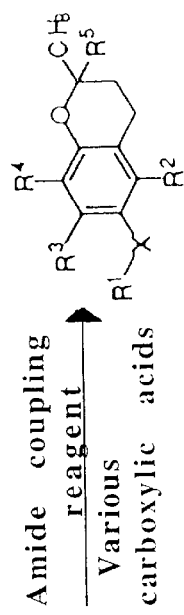
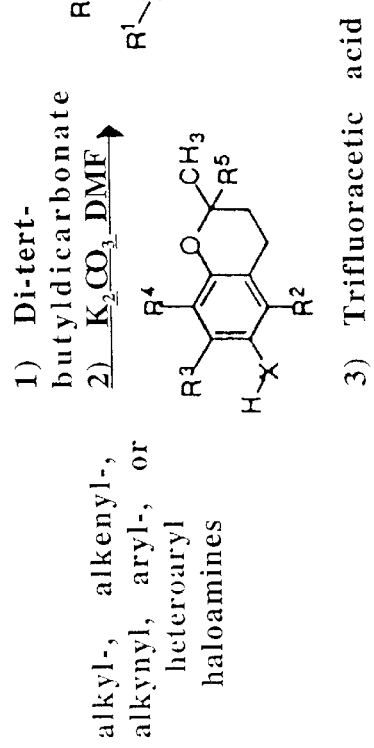
Fig. 3D

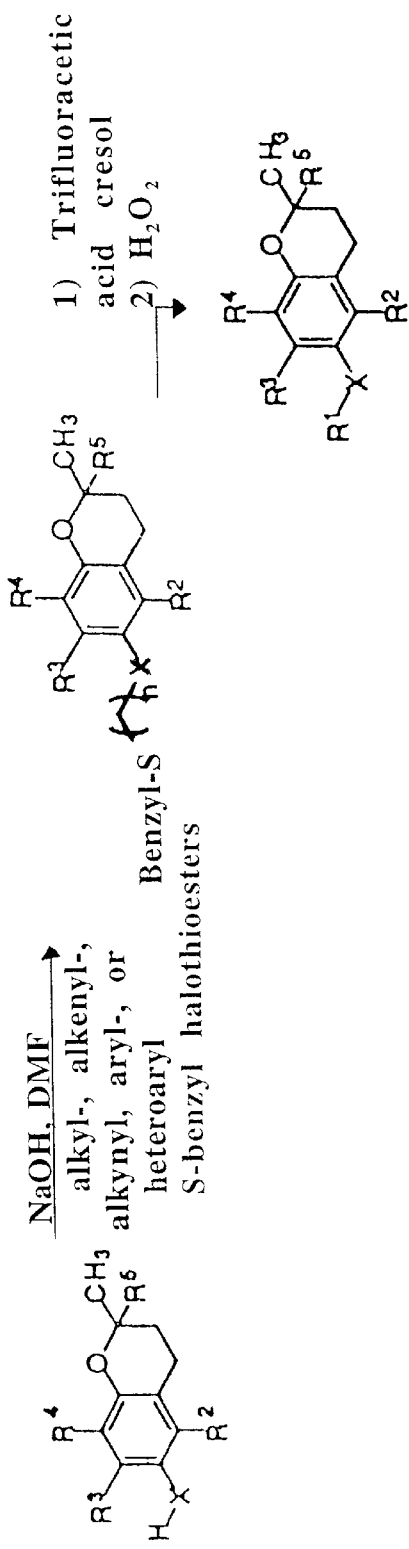
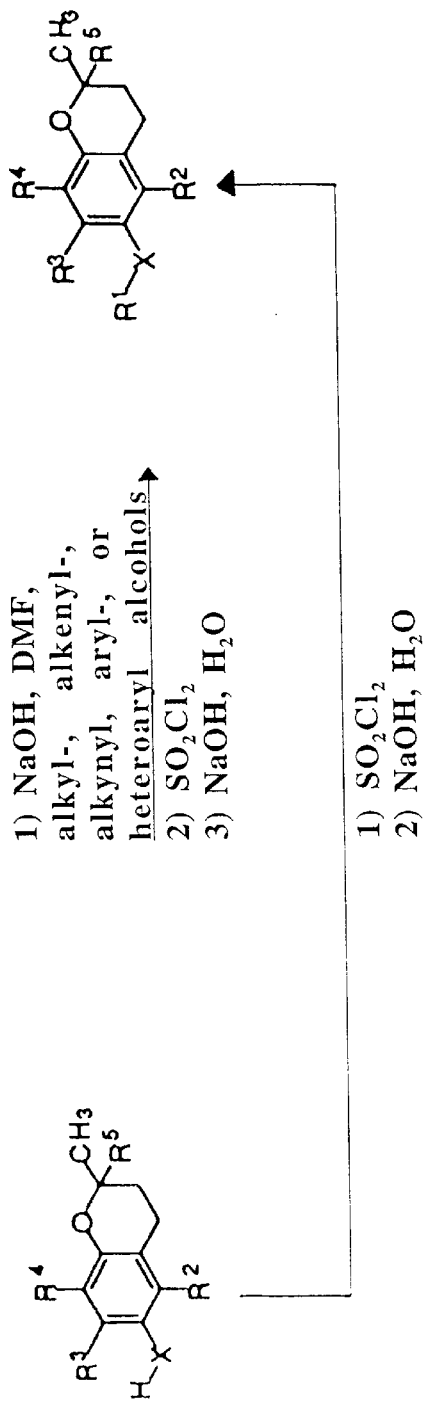
Fig. 3E

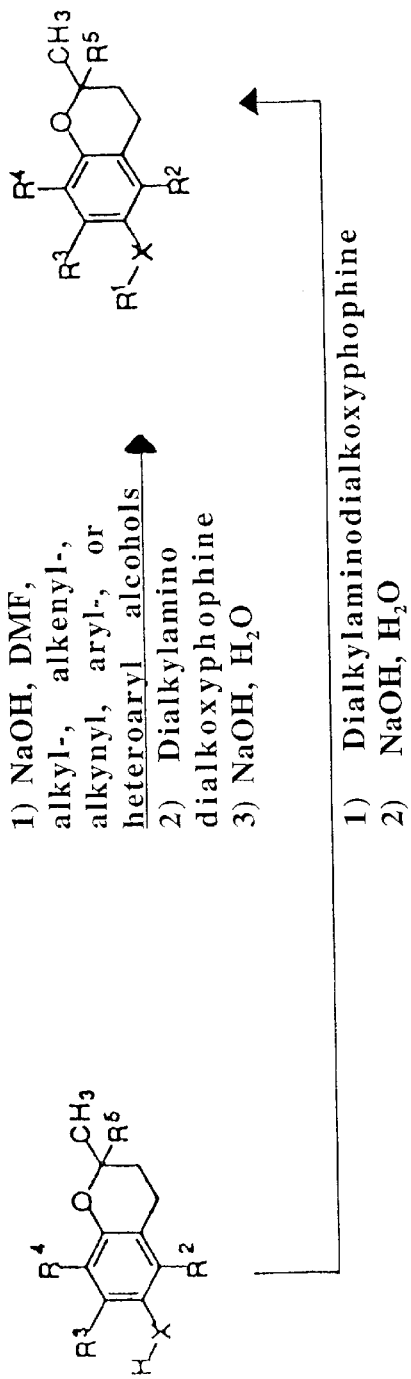
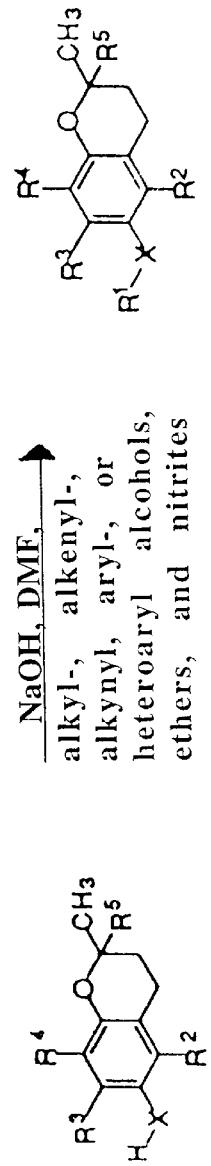
Fig. 3F

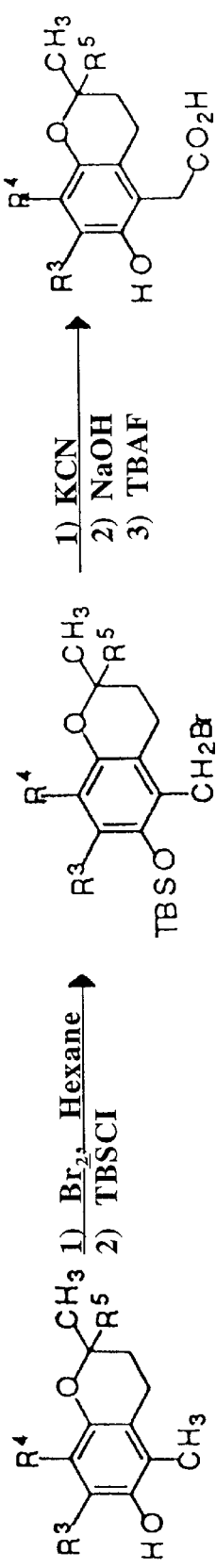
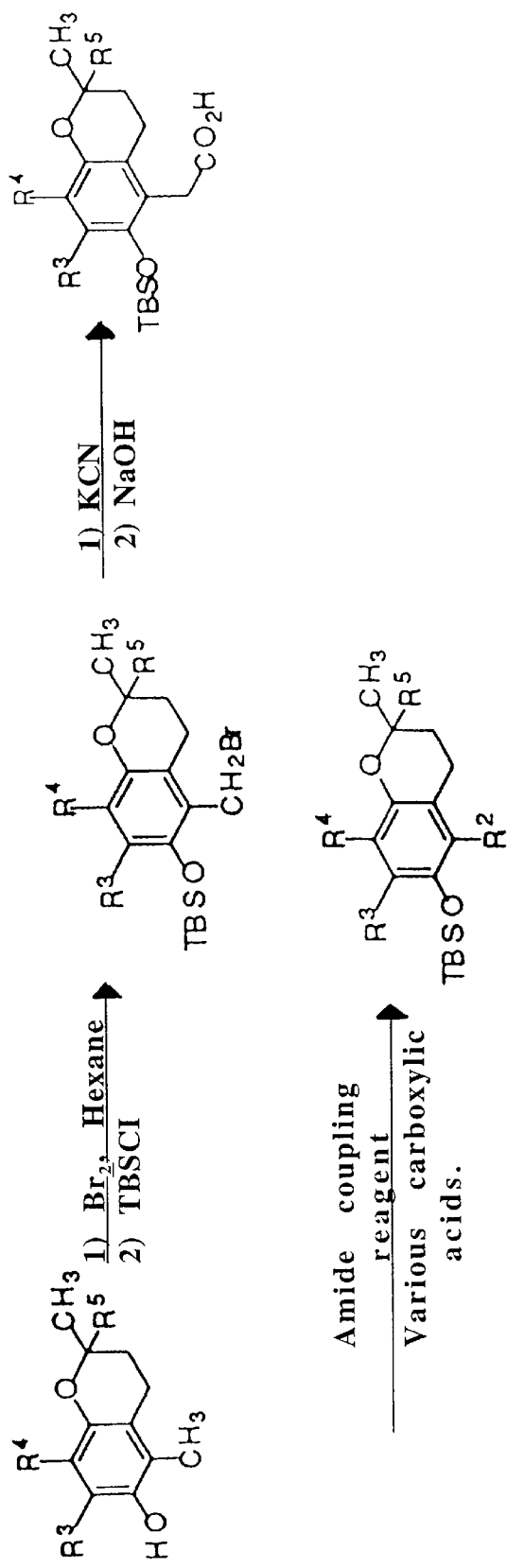
Fig. 4A

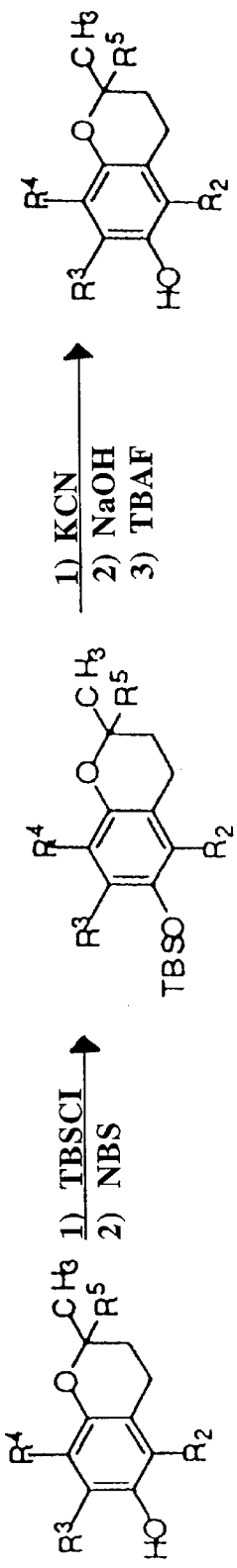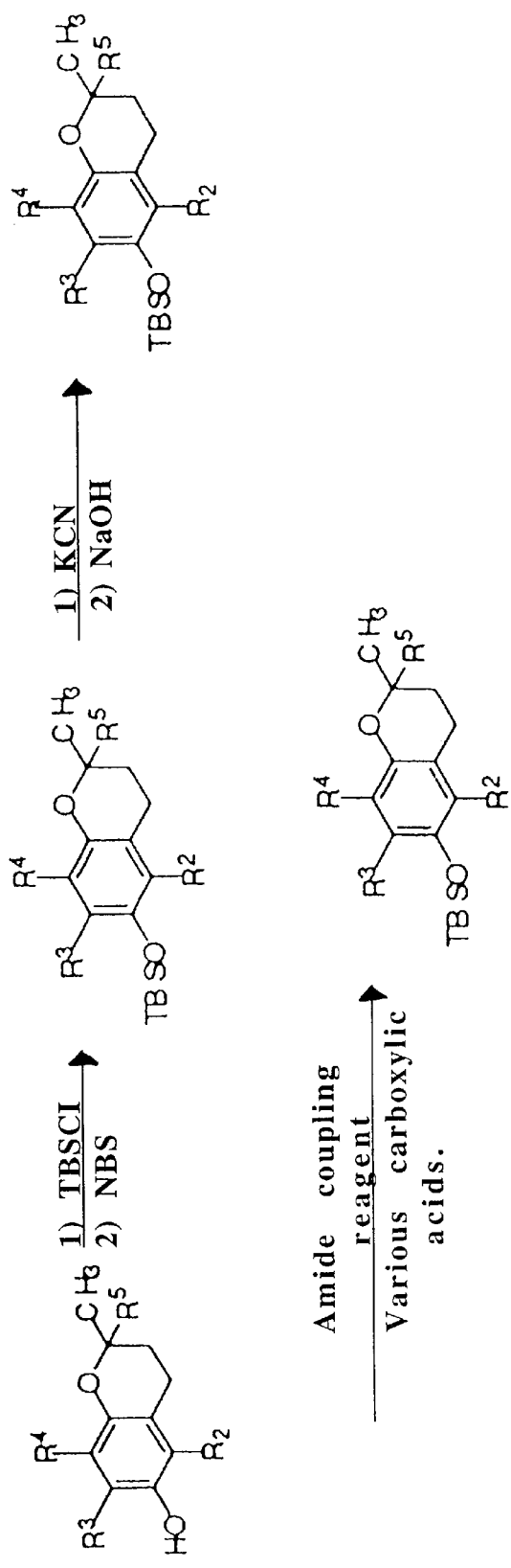
Fig. 5A

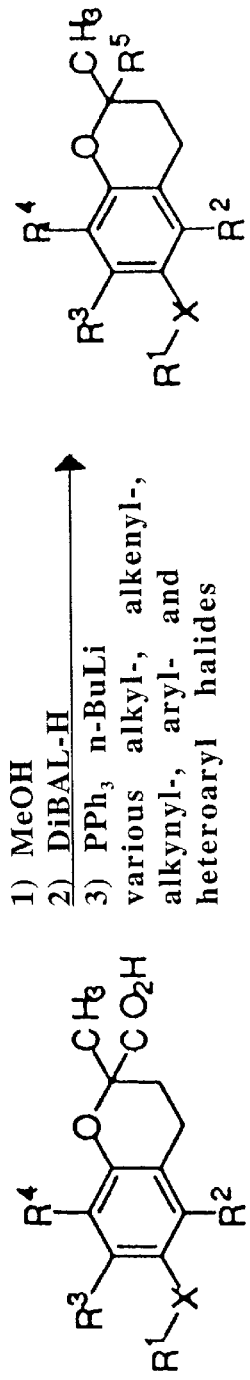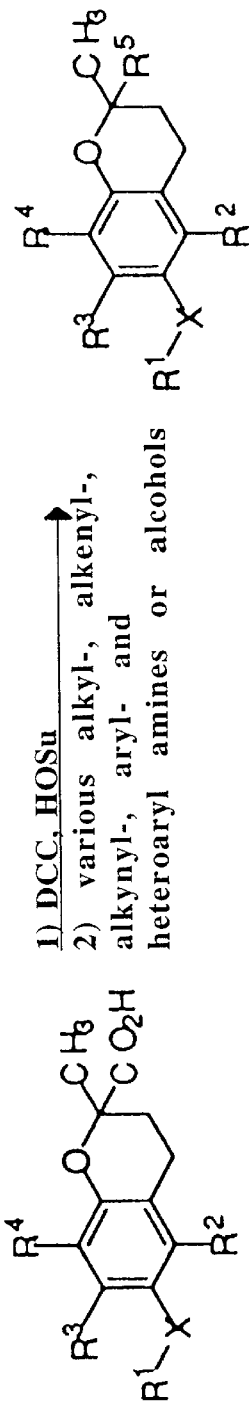
Fig. 6

TOCOPHEROLS, TOCOTRIENOLS, OTHER CHROMAN AND SIDE CHAIN DERIVATIVES AND USES THEROF

CROSS-REFERENCE TO RELATED APPLICATIONS

This patent application claims benefit of provisional application U.S.S.N. 60/101,542, filed Sep. 23, 1998, now abandoned.

BACKGROUND OF THE INVENTION

1. Field of the Invention

The present invention relates generally to the fields of organic chemistry and antiproliferative and pro-apoptotic compounds. More specifically, the present invention relates to chroman-based compounds and derivatives thereof, and their uses as cell anti-proliferative, proapoptotic, immunomodulating, and anti-viral agents.

2. Description of the Related Art

The biology of cell proliferation and cell death (apoptosis) is extremely complex, involving multiple intracellular signaling pathways and multiple interacting gene products. Cancer cells may exhibit multiple defects in normal regulatory controls of cell proliferation which allow them to increase in number. Furthermore, cancer cells exhibit defects in mechanisms that are involved in eliminating abnormal cells by multi-step processes referred to as programmed cell death or apoptosis. Thus, combinations of unregulated cell proliferation and suppression of death inducing signaling pathways give cancer cells both growth and survival advantages.

Whether a cell increases in numbers or not depends on a balance of expression of negatively-acting and positively-acting growth regulatory gene products, and the presence or absence of functional cell death signaling pathways. Negative-acting growth regulatory genes contribute to blockage of cells in the cell cycle. Positive-acting growth regulatory genes stimulate cells to progress through the cell cycle. Genes involved in apoptosis can be either proapoptotic or antiapoptotic, and the dynamic balance between them determines whether a cell lives or dies.

Cancer cells, in order to survive and increase their numbers, undergo a series of mutational events over time that remove regulatory controls that give them the ability to grow unchecked and survive even in the presence of proapoptotic signals, and develop attributes that permit them to escape detection and removal by the immune response defense system. Cancers may cause death of individuals unless removed by surgery or effectively treated with drugs.

A wide variety of pathological cell proliferative conditions exist for which novel therapeutic strategies and agents are needed to provide therapeutic benefits. These pathological conditions may occur in almost all cell types capable of abnormal cell proliferation or abnormal responsiveness to cell death signals. Among the cell types that exhibit pathological or abnormal growth and death characteristics are (1) fibroblasts, (2) vascular endothelial cells, and (3) epithelial cells. Thus, novel methods are needed to treat local or disseminated pathological conditions in all or almost all organ and tissue systems of individuals.

Most cancers, whether they be male specific such as prostate or testicular, or female specific such as breast, ovarian or cervical or whether they affect males and females equally such as liver, skin or lung, with time undergo increased genetic lesions and epigenetic events, and eventually become highly metastatic and difficult to treat. Surgical removal of localized cancers has proven effective only when the cancer has not spread beyond the primary lesion. Once the cancer has spread to other tissues and organs, the surgical procedures must be supplemented with other more specific procedures to eradicate the diseased or malignant cells. Most of the commonly utilized supplementary procedures for treating diseased or malignant cells such as chemotherapy or bioradiation are not localized to the tumor cells and, although they have a proportionally greater destructive effect on malignant cells, often affect normal cells to some extent.

Some derivatives of tocopherols, tocotrienols and vitamin E have been used as proapoptotic and DNA synthesis inhibiting agents. Structurally, vitamin E is composed of a chromanol head and an alkyl side chain. There are eight major naturally occurring forms of vitamin E alpha ($\alpha$), beta ($\beta$), gamma ($\gamma$), and delta ($\delta$) tocopherols and $\alpha$, $\beta$, $\gamma$, and $\delta$ tocotrienols. Tocopherols differ from tocotrienols in that they have a saturated phytyl side chain rather than an unsaturated isoprenyl side chain. The four forms of tocopherols and tocotrienols differ in the number of methyl groups on the chromanol head (a has three, $\beta$ and $\gamma$ have two and $\delta$ has one).

RRR-$\alpha$-tocopheryl succinate is a derivative of RRR-$\alpha$-tocopherol that has been structurally modified via an ester linkage to contain a succinyl moiety instead of a hydroxyl moiety at the 6-position of the chroman head. This ester linked succinate moiety of RRR-$\alpha$-tocopherol has been the most potent form of vitamin E affecting the biological actions of triggering apoptosis and inhibiting DNA synthesis. This form of vitamin E induces tumor cells to undergo apoptosis, while having no apoptotic inducing effects on normal cells. The major advantage of this form of vitamin E as an anticancer agent is that many cancer cells either express low levels of esterases or do not express esterases that can cleave the succinate moiety, thereby converting the succinate form of RRR-$\alpha$-tocopherol to the free RRR-$\alpha$-tocopherol. RRR-$\alpha$-tocopherol exhibits neither potent antiproliferative nor apoptotic triggering biological activity. However, the ester-linked vitamin E succinate is ineffective in vivo since natural esterases in the host cleave off the succinate moiety, rendering an ineffective anticancer agent, RRR-$\alpha$-tocopherol.

The prior art is deficient in the lack of effective means of inhibiting undesirable or uncontrollable cell proliferation in a wide variety of pathophysiological conditions while having no to little effect on normal cells. The present invention fulfills this long-standing need and desire in the art.

SUMMARY OF THE INVENTION

In one embodiment of the present invention, there is provided a compound having a structural formula

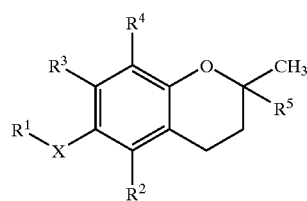

wherein X is oxygen, nitrogen or sulfur; $R^1$ is selected from the group consisting of alkyl, alkenyl, alkynyl, aryl, heteroaryl, carboxylic acid, carboxylate, carboxamide, ester, thioamide, thiolester, thiolacid, saccharide, alkoxy-linked saccharide, amine, sulfonate, sulfate, phosphate, alcohol, ether and nitrile; $R^2$ is selected from the group consisting of hydrogen, methyl, benzyl carboxylic acid, benzyl carboxylate, benzyl carboxamide, benzyl ester, saccharide and amine; $R^3$ is selected from the group consisting of hydrogen, methyl, benzyl carboxylic acid, benzyl carboxylate, benzyl carboxamide, benzylester, saccharide and amine; $R^4$ is selected from the group consisting of methyl, benzyl carboxylic acid, benzyl carboxylate, benzyl carboxamide, benzylester, saccharide and amine; and $R^5$ is selected from the group consisting of alkyl, alkenyl, alkynyl, aryl, heteroaryl, carboxyl, amide and ester; wherein when X is oxygen, $R^2$ is methyl, $R^3$ is methyl, $R^4$ is methyl and $R^5$ is phytyl, $R^1$ is not butyric acid.

In another embodiment of the present invention, there is provided a method for the treatment of a cell proliferative disease comprising administering to an animal a pharmacologically effective dose of a compound having a structural formula

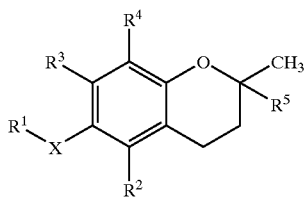

wherein X is oxygen, nitrogen or sulfur; $R^1$ is selected from the group consisting of alkyl, alkenyl, alkynyl, aryl, heteroaryl, carboxylic acid, carboxylate, carboxamide, ester, thioamide, thiolester, thiolacid, saccharide, alkoxy-linked saccharide, amine, sulfonate, sulfate, phosphate, alcohol, ether and nitrile; $R^2$ is selected from the group consisting of hydrogen, methyl, benzyl carboxylic acid, benzyl carboxylate, benzyl carboxamide, benzyl ester, saccharide and amine; $R^3$ is selected from the group consisting of hydrogen, methyl, benzyl carboxylic acid, benzyl carboxylate, benzyl carboxamide, benzylester, saccharide and amine; $R^4$ is selected from the group consisting of methyl, benzyl carboxylic acid, benzyl carboxylate, benzyl carboxamide, benzylester, saccharide and amine; and $R^1$ is selected from the group consisting of alkyl, alkenyl, alkynyl, aryl, heteroaryl, carboxyl, amide and ester.

In yet another embodiment of the present invention, there is provided a pharmaceutical composition comprising a compound disclosed herein and a pharmaceutically acceptable carrier.

In yet another embodiment of the present invention, there is provided a method of inducing apoptosis of a cell, comprising the step of contacting said cell with a pharmacologically effective dose of a compound of the present invention.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. above may be had by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIGS. 2A and 2B show general tocopherol-based compounds 1–29 presently synthesized and tested.

FIGS. 3A–3F show general synthetic organic approaches for the chemical variation of chromanol compounds at position $R^1$.

FIGS. 4A and 4B show general synthetic organic approaches for the chemical variation of chromanol compounds at position $R^2$.

FIGS. 5A and 5B show general synthetic organic approaches for the chemical variation of chromanol compounds at position $R^3$ and $R^4$.

FIG. 6 shows general synthetic organic approaches for the chemical variation of chromanol compounds at position $R^5$.

DETAILED DESCRIPTION OF THE INVENTION

As used herein, the term "individual" shall refer to animals and humans.

As used herein, the term "biologically inhibiting" or "inhibition" of the growth of proliferating cells shall include partial or total growth inhibition and also is meant to include decreases in the rate of proliferation or growth of the cells. The biologically inhibitory dose of the composition of the present invention may be determined by assessing the effects of the test element on target malignant or abnormally proliferating cell growth in tissue culture, tumor growth in animals and cell culture or any other method known to those of ordinary skill in the art.

As used herein, the term "induction of programmed cell death or apoptosis" shall include partial or total cell death with cells exhibiting established morphological and biochemical apoptotic characteristics. The dose of the composition of the present invention that induces apoptosis may be determined by assessing the effects of the test element on target malignant or abnormally proliferating cell growth in tissue culture, tumor growth in animals and cell culture or any other method known to those of ordinary skill in the art.

As used herein, the term "induction of cell cycle arrest" shall include growth arrest due to treated cells being blocked in G0/G1 or G2/M cell cycle phase. The dose of the composition of the present invention that induces cell cycle arrest may be determined by assessing the effects of the test element on target malignant or abnormally proliferating cell growth in tissue culture, tumor growth in animals and cell culture or any other method known to those of ordinary skill in the art.

As used herein, the term "induction of cellular differentiation" shall include growth arrest due to treated cells being induced to undergo cellular differentiation, a stage in which cellular proliferation does not occur. The dose of the composition of the present invention that induces cellular differentiation may be determined b y assessing the effects of the test element on target malignant or abnormally proliferating cell growth in tissue culture, tumor growth in animals and cell culture or any other method known to those of ordinary skill in the art.

Figure 1:
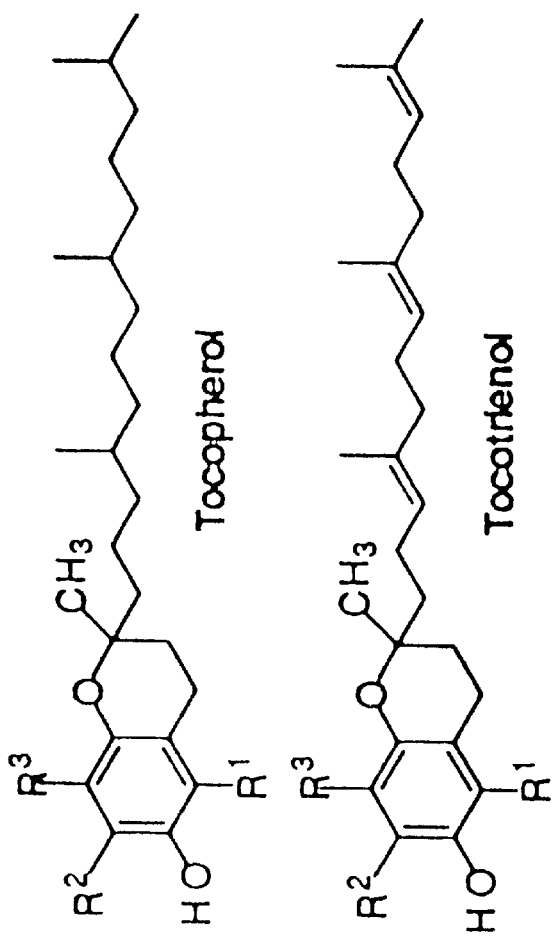
FIG. 1 shows general structure of tocopherol, tocotrienol and other chroman-based compounds.
Figure 3C:
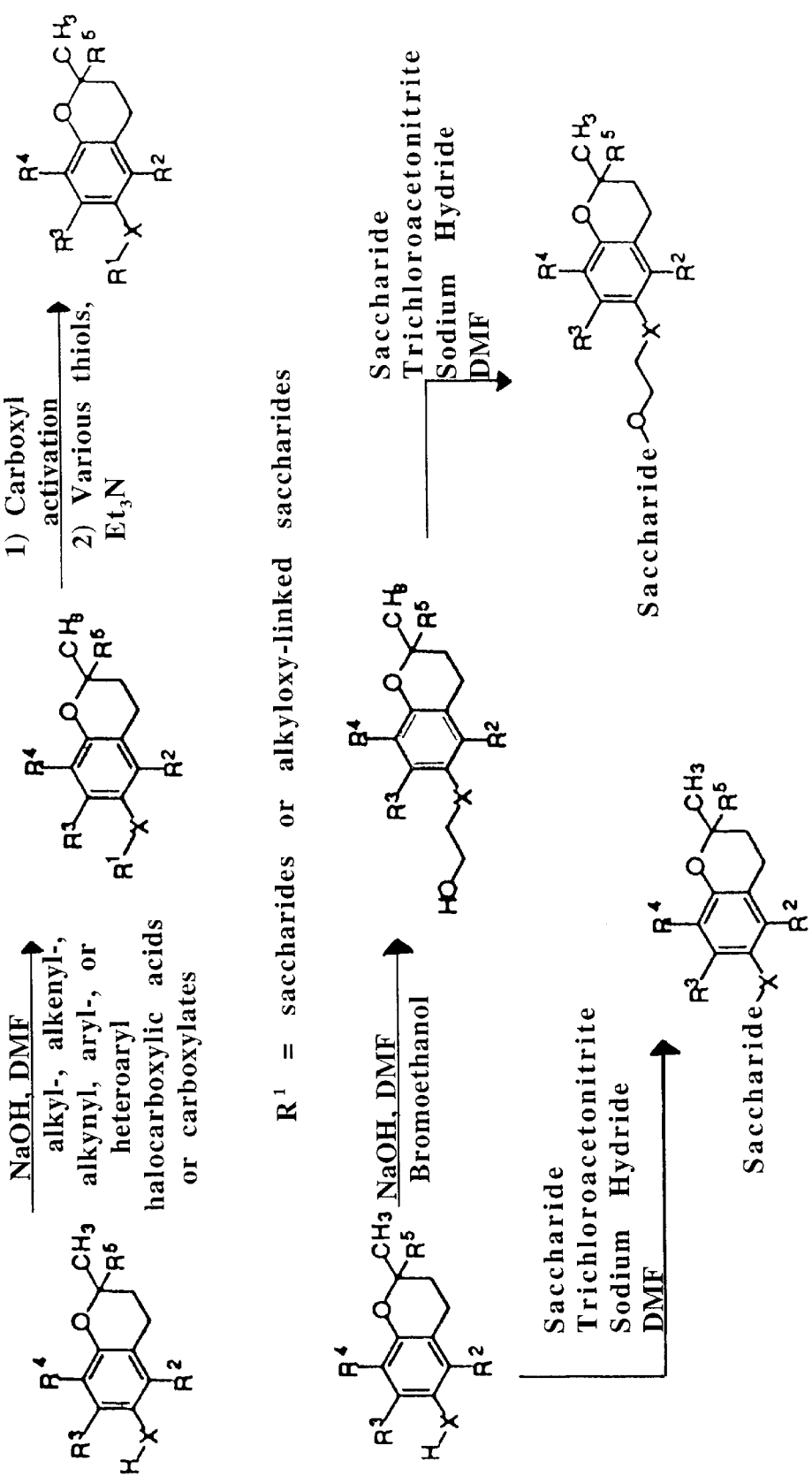
Figure 4B:
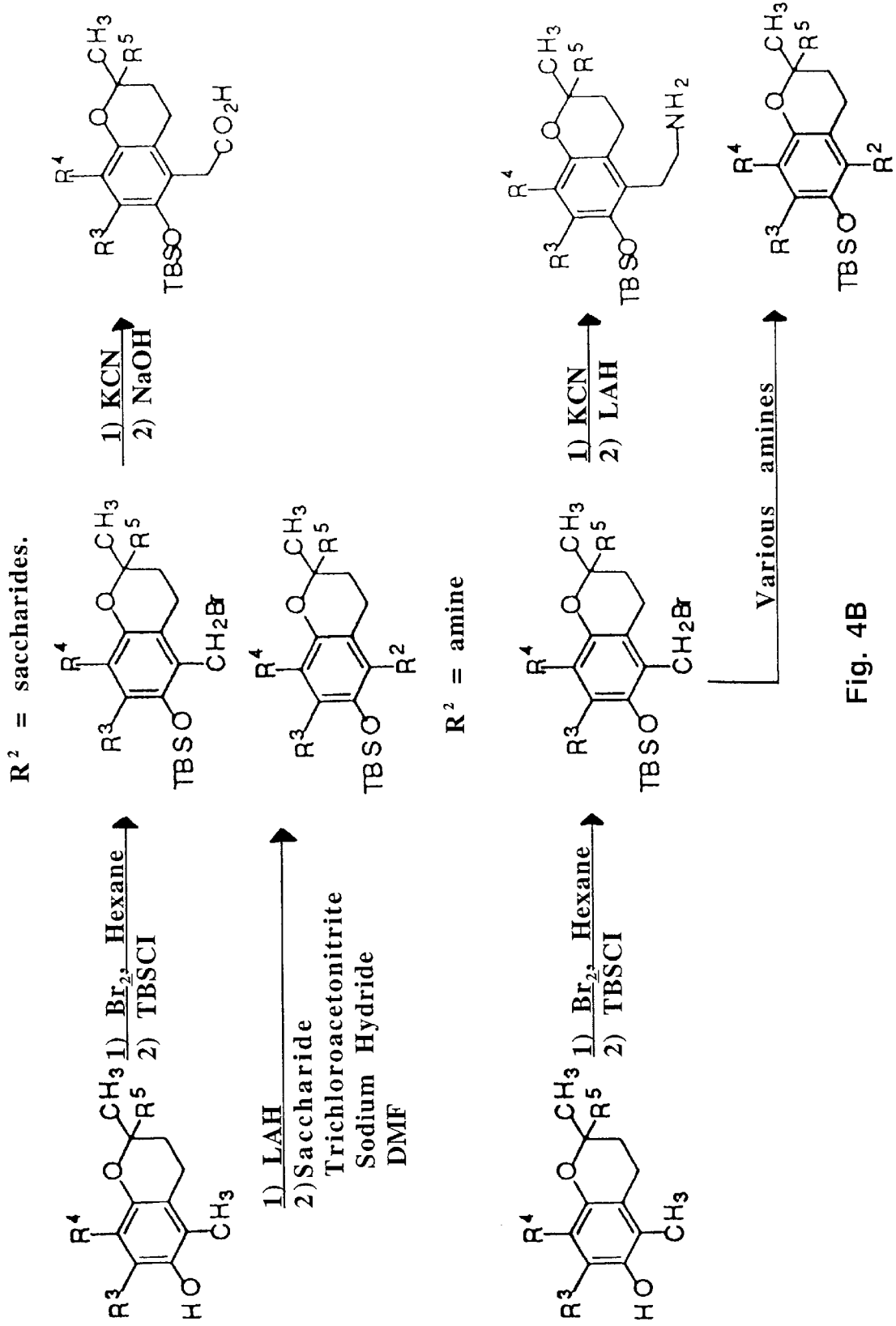
Figure 5B:
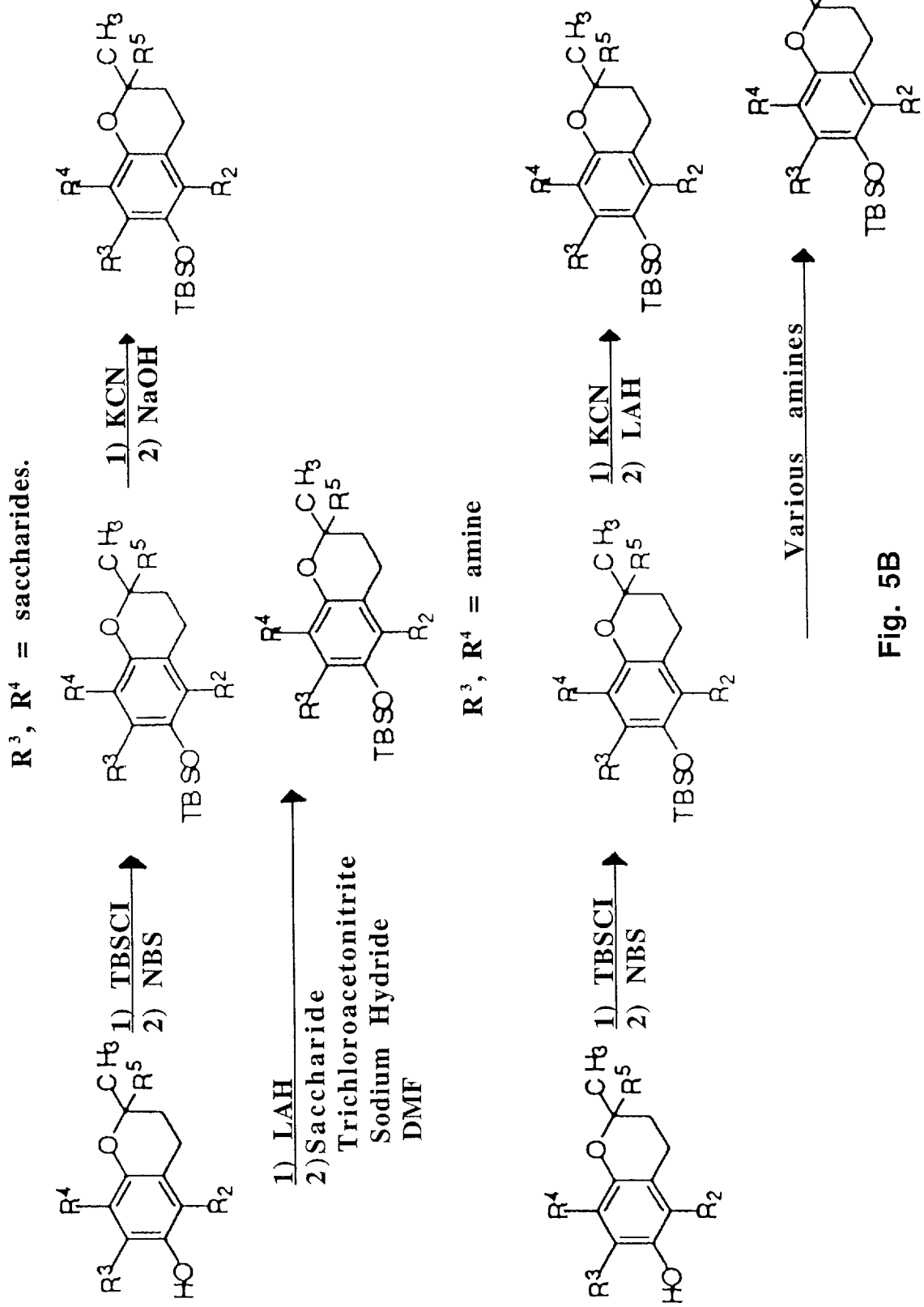

The present invention provides tocopherols, tocotrienols, and other chroman derivatives with or without derivatives of saturated phytyl or unsaturated isoprenyl side chains and analogs thereof. Utilizing ethers and several other chemical linkages to attach different moieties to tocopherol, tocotrienol and other chroman derivatives, novel anti-cancer compounds, for in vivo use, are produced. The general structures of the novel compounds of the present invention are shown in FIG. 1 and possible routes for their syntheses are provided in FIGS. 3–6. The novel features of these molecules include chemical functionalization of positions $R^1$–$R^5$ of the chroman structure, and chemical functionalization of the phytyl and isoprenyl side chains, particularly compounds based on tocopherols and tocotrienols (FIG. 1). Particularly preferred compounds include 2,5,7,8-tetramethyl-(2R-(4R,8R,12-trimethyltridecyl)chroman-6-yloxy)acetic acid (1), 2,5,7,8-tetramethyl-(2R-(4R,8R,12-trimethyltridecyl)chroman-6-yloxy)propionic acid (2), 2,5,8-trimethyl-(2R-(4R,8R,12-trimethyltridecyl)chroman-6-yloxy)acetic acid (7), 2,7,8-trimethyl-(2R-(4R,8R,12-trimethyltridecyl)chroman-6-yloxy)acetic acid (8), 2,8-dimethyl-(2R-(4R,8R,12-trimethyltridecyl)chroman-6-yloxy)acetic acid (9), 2-(N,N-(carboxymethyl)-2(2,5,7,8-tetramethyl-(2R-(4R,8R,12-trimethyltridecyl)chroman-6-yloxy)acetic acid (12), 2,5,7,8-tetramethyl-(2RS-(4RS,8RS,12-trimethyltridecyl)chroman-6-yloxy)acetic acid (15), 2,5,7,8-tetramethyl-2R-(2RS,6RS, 10-trimethylundecyl)chroman-6-yloxy)acetic acid (17), 3-(2,5,7,8-tetramethyl-(2R-(4R,8,12-trimethyltridecyl)chroman-6-yloxy)propyl-1-ammonium chloride (19), 2,5,7,8-tetramethyl-(2R-(4r,8R, 12-trimethyltridecyl)chroman-3-ene-6-yloxy)acetic acid (20), 2-(2,5,7,8-tetramethyl-(2R-(4R,8,12-trimethyltridecyl)chroman-6-yloxy)triethylammonium sulfate (21), 6-(2,5,7, 8-tetramethyl-(2R-(4R,8,12-trimethyltridecyl)chroman) acetic acid (22), 2,5,7,8,-tetramethyl-(2R-(heptadecyl) chroman-6-yloxy)acetic acid (25), 2,5,7,8,-tetramethyl-2R-(4,8,-dimethyl-1,3,7 EZ nonotrien)chroman-6-yloxy)acetic acid (26), and E,Z,RS,RS-(phytyltrimethylbenzenethiol-6-yloxy)acetic acid (27).

The pharmacodynamically designed compounds of the present invention have an improved therapeutic index and are potent inhibitors of cancer cell growth; i.e., they demonstrate high antitumor activity with minimal side effects. These compounds, which can not be readily degraded since there are no known etherases in mammals, may be used in the treatment of cancers and disorders involving excess cell proliferation, as well as for cells that accumulate in numbers due to suppressed cell killing mechanisms, with minimal side effects. The compounds of the present invention inhibit cancer cell growth by induction of apoptosis and DNA synthesis arrest. Induction of apoptosis by these compounds is mediated by activation of the TGF-β, stress kinase, and Fas/Fas ligand signaling pathways. Induction of apoptosis by other pathways, for example, ceramide production, are not excluded. These growth inhibitory properties allow these compounds to be used in the treatment of proliferative diseases, including cancers of different cell types and lineages, non-neoplastic hyperproliferative diseases, and disorders with defects in apoptotic signaling pathways. Several of the compounds of the present invention are both strong inducers of apoptosis and strong inhibitors of DNA synthesis arrest of tumor cells representing different cellular lineages.

The therapeutic use of the compounds of the present invention in treatment of cancers and other diseases and disorders involving excess cell proliferation or failure of cells to die is illustrated. The novel derivatives (Tables 1 and 2) were shown at $EC_{50}$ concentrations to induce apoptosis of human breast cancer cells (MDA MB 435, MDA MB 231, and MCF-7 breast cancer cells), human prostate cancer cells (PC-3, DU-145 and LnCaP), human ovarian tumor cells (C-170), human cervical tumor cells (ME-180), human endometrial cells (RL-95-2), human lymphoid cells (myeloma, Raji, Ramos, Jurkat, and HL-60), colon cancer cells (HT-29 and DLD-1) and lung cancer cells (A-549). The novel derivatives were shown to not induce apoptosis of normal human mammary epithelial cells (HMECS) and immortalized but non-tumorigenic MCF-10A mammary cells.

These novel compounds and methods of the present invention may be used to treat neoplastic diseases and non-neoplastic diseases. Representative examples of neoplastic diseases are ovarian cancer, cervical cancer, endometrial cancer, bladder cancer, lung cancer, cervical cancer, breast cancer, prostate cancer, testicular cancer, gliomas, fibrosarcomas, retinoblastomas, melanomas, soft tissue sarcomas, osteosarcomas, colon cancer, carcinoma of the kidney, pancreatic cancer, basal cell carcinoma, and squamous cell carcinoma. Representative examples of non-neoplastic diseases are selected from the group consisting of psoriasis, benign proliferative skin diseases, ichthyosis, papilloma, restinosis, scleroderma and hemangioma.

The compounds and methods of the present invention may be used to treat non-neoplastic diseases that develop due to failure of selected cells to undergo normal programmed cell death or apoptosis. Representative examples of diseases and disorders that occur due to the failure of cells to die are autoimmune diseases. Autoimmune diseases are characterized by immune cell destruction of self cells, tissues and organs. A representative group of autoimmune diseases includes autoimmune thyroiditis, multiple sclerosis, myasthenia gravis, systemic lupus erythematosus, dermatitis herpetiformis, celiac disease, and rheumatoid arthritis. This invention is not limited to autoimmunity, but includes all disorders having an immune component, such as the inflammatory process involved in cardiovascular plaque formation, or ultra violet radiation induced skin damage.

The compounds and methods of the present invention may be used to treat disorders and diseases that develop due to virus infections. Representative examples of diseases and disorders that occur due to virus infections are human immunodeficiency viruses (HIV). Since these compounds are working on intracellular signaling networks, they have the capacity to impact on any type of external cellular signal such as cytokines, viruses, bacteria, toxins, heavy metals, etc.

The methods of the present invention may be used to treat any animal. Most preferably, the methods of the present invention are useful in humans.

Generally, to achieve pharmacologically efficacious cell killing and anti-proliferative effects, these compounds and analogs thereof may be administered in any therapeutically effective dose. Preferably, the structurally modified tocopherols and tocotrienols and analogs are administered in a dose of from about 0.1 mg/kg to about 100 mg/kg. More preferably, the structurally modified tocopherols and tocotrienols and analogs are administered in a dose of from about 1 mg/kg to about 10 mg/kg.

Administration of the compositions of the present invention may be by topical, intraocular, parenteral, oral, intranasal, intravenous, intramuscular, subcutaneous, or any other suitable means. The dosage administered is dependent upon the age, clinical stage and extent of the disease or genetic predisposition of the individual, location, weight, kind of concurrent treatment, if any, and nature of the pathological or malignant condition. The effective delivery system useful in the method of the present invention may be employed in such forms as capsules, tablets, liquid solutions, suspensions, or elixirs, for oral administration, or sterile liquid forms such as solutions, suspensions or emulsions. For topical use it may be employed in such forms as ointments, creams or sprays. Any inert carrier is preferably used in combination with suitable solubilizing agents, such as saline, or phosphate-buffered saline, or any such carrier in which the compounds used in the method, such as ethanol, acetone, or DMSO, of the present invention have suitable solubility properties.

There are a wide variety of pathological cancerous and noncancerous cell proliferative conditions and cell accumulations due to absence of normal cellular death for which the compositions and methods of the present invention will provide therapeutic benefits. These pathological conditions may occur in almost all cell types capable of abnormal cell proliferation or defective in programmed cell death mechanisms. Among the cell types which exhibit pathological or abnormal growth or abnormal death are (1) fibroblasts, (2) vascular endothelial cells and (3) epithelial cells. It can be seen from the above that the methods of the present invention is useful in treating local or disseminated pathological conditions in all or almost all organ and tissue systems of individuals.

It is specifically contemplated that pharmaceutical compositions may be prepared using the novel chroman-based compounds and derivatives thereof of the present invention. In such a case, the pharmaceutical composition comprises the novel compounds of the present invention and a pharmaceutically acceptable carrier. A person having ordinary skill in this art would readily be able to determine, without undue experimentation, the appropriate dosages and routes of administration of the compounds and analogs of the present invention.

Thus the present invention is directed toward the design and effective use of novel agents that can specifically target cancer cells and either down-regulate growth stimulatory signals, up-regulate growth inhibitory signals, down-regulate survival signals and/or up-regulate death signals. More specifically, this invention creates and characterizes novel agents that activate growth inhibitory factors, trigger death signaling pathways, and inhibit DNA synthesis.

The following examples are given for the purpose of illustrating various embodiments of the invention and are not meant to limit the present invention in any fashion.

EXAMPLE 1

Synthetic Organic Methodology

The synthesis of a variety of tocopherol, tocotrienol, and other chroman derivatives with or without derivatives of saturated phytyl or unsaturated isoprenyl side chains is possible via structural modification of the chroman ring system (FIGS. 3–6). The structural variables $R^1$, $R^2$, $R^3$, $R^4$, $R^5$, and X illustrate the groups on the chroman group that are modified. Using alkylation chemistry, a large number of compounds containing different $R^1$ groups can be synthesized, particularly when X is oxygen. After alkylation, further chemical modification of the $R^1$ groups permits the synthesis of a wide range of novel compounds. Bromination of the benzylic methyl groups of the chroman group provide intermediates that permit variation of the $R^2$, $R^3$ and $R^4$ groups. Variation of group $R^5$ is also possible, particularly when starting from the commercially available 6-hydroxy-2,5,7,8-tetramethylchroman-2-carboxylic acid. Variation of X to groups other than oxygen, which is the identity of X in tocopherols and tocotrienols, can be accomplished using palladium chemistry (for X=CH$_2$) and nucleophilic aromatic substitution (for X=N or S). Other possible modifications to the chroman structure include unsaturation at the 3–4 positions, ring contraction to produce a five-membered furanyl ring, and heteroatom substitutions (N or S) for the chroman ring oxygen.

Reagents employed were either commercially available or prepared according to a known procedure. Anhydrous CH$_2$Cl$_2$ and THF were obtained by distillation. All other solvents used were reagent. Anhydrous reaction conditions were maintained under a slightly positive argon atmosphere in oven-dried glassware. Silica gel chromatography was performed using 230–400 mesh silica purchased from EM Science. Routine $^1$H- and $^{13}$C-NMR spectra were obtained on a Varian Unity spectrometer at 300.132 MHz and 75.033 MHz frequencies, respectively. NMR spectra were referenced to TMS (0 ppm) or to the isotopic impurity peak of CDCl$_3$ (7.26 and 77.0 ppm for $^1$H and $^{13}$C, respectively). High resolution electron impact ionization mass spectroscopy was performed by the Mass Spectrometry Center at The University of Texas at Austin.

EXAMPLE 2

Synthesis and Characterization of Novel Tocopherol Compounds 2,5,7,8-Tetramethyl-(2R-(4R,8R,12-trimethyltridecyl) chroman-6-yloxy)acetic Acid (1)

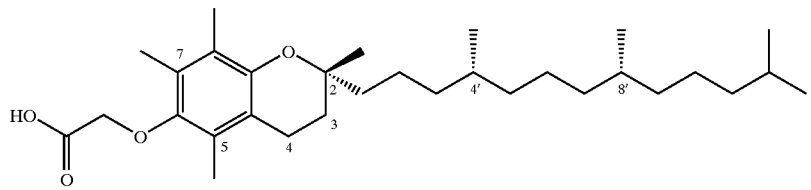

A solution of R,R,R-α-tocopherol (0.5 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 1 as a waxy, off-white solid (0.50 g, 88%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-,12'-CH, 1'-,2'-,3'-,5'-6'-,7'-, 9'-,10'-,11'-CH$_2$, 2a-CH$_3$), 1.81 (m, 2H, 3-CH$_2$), 2.07, 2.14, 2.16 (3×s, 9H, 5a-, 7a-, 8a-CH$_3$), 2.59 (t, J=6.6 Hz, 2H, 4-CH$_2$), 4.34 (s, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 37.3, 37.4, 37.5, 39.4, 40.0 (CH$_2$), 69.2 (OCH$_2$), 75.0 (2-C), 117.8, 123.2, 125.4, 127.3 (aryl C), 147.0, 148.5 (aryl C—O), 173.7 (COOH); HRMS (CI, m/z): 489.394374 (M+H$^+$, Calc. for C$_{31}$H$_{53}$O$_4$ 489.394386). All assignments were confirmed using HMQC, DEPT-135, and $^1$H-NOSEY.

2,5,7,8-Tetramethyl-(2R-(4R,8R 12-trimethyltridecyl) chroman-6-yloxy)propionic Acid (2)

The compounds 2–6 are synthesized in a manner identical to the synthesis of 1 using the appropriate bromoalkanoic acids.

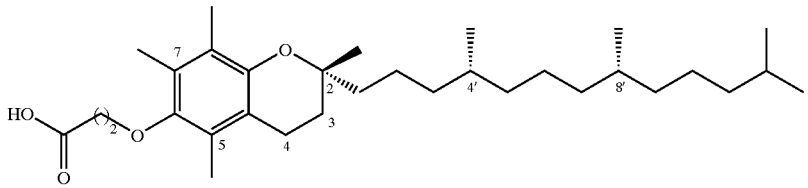

(89% yield). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-,5'-,6'-,7'-,9'-,10'-,11'-CH$_2$, 2a-CH$_3$), 1.81 (m, 2H, 3-CH$_2$), 2.09, 2.14, 2.19 (3×s, 9H, 5a-, 7a-, 8a-CH$_3$), 2.59 (t, J=6.6 Hz, 2H, 4-CH$_2$), 2.85 (t, J 6.4 Hz, 2H, CH$_2$COOH), 3.96 (t, J=6.4 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 35.1, 37.3, 37.4, 37.5, 39.4, 40.0 (CH$_2$), 67.5 (OCH$_2$), 74.8 (2-C), 117.5, 122.9. 125.8, 127.8 (aryl C), 147.6, 148.0 (aryl C—O), 177.1 (COOH); HRMS (CI, m/z): 503.408610 (M+H$^+$, Calc. for C$_{32}$H$_{55}$O$_4$ 503.410036).

2,5,7,8-Tetramethyl-(2R-(4R,8R,12-trimethyltridecyl) chroman-6-yloxy)butyric Acid (3)

(90% yield). $^1$H-NMR (CDCl$_3$/TMS, ppm): 0.87 (m, 12H, 4a'-, 8a'-, 12a'-, 13'-CH$_3$), 1.0–1.6 (m, 28H, 4'-, 8'-,12'-CH, 1'-,2'-,3'-,5'-,6'-,7'-,9'-,10'-,11'-CH$_2$, 2a-CH$_3$), 1.81 (m, 2H, 3-CH$_2$), 2.09, 2.14, 2.18 (3×s, 9H, 5a-, 7a-, 8a-CH$_3$), 2.49 (t, J=6.8 Hz, 2H, CH$_2$COOH), 2.59 (t, J=6.6 Hz, 2H, 4-CH$_2$), 3.68 (t, J=5.5 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0, 21.4 (CH$_2$), 22.6, 22.7 (CH$_3$), 23.8 (2a-CH$_3$), 24.4, 24.8 (CH$_2$), 28.0 (CH), 30.0 (CH$_2$), 31.2 (3-CH$_2$), 32.7, 32.8 (CH), 35.8, 37.3, 37.4, 37.5, 39.4, 40.0 (CH$_2$), 72.2 (OCH$_2$), 74.9 (2-C), 117.8, 123.2. 125.4, 127.3 (aryl C), 147.6, 148.3 (aryl C—O), 178.7 (COOH); HRMS (CI, m/z): 530.433514 (M+H$^+$, Calc. for C$_{34}$H$_{59}$O$_4$ 530.433516).

2,5,7,8-Tetramethyl-2R-(4R,8R,12-trimethyltridecyl) chroman-6-yloxy)hexanoic Acid (5)

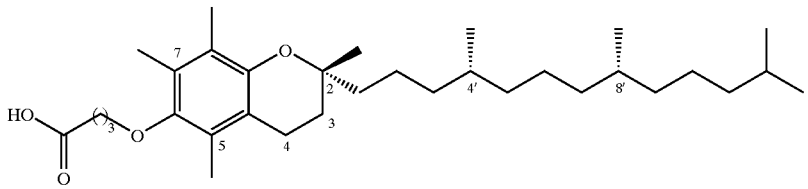

(85% yield). $^1$H-NMR (CDCl$_3$/TMS, ppm): 0.87 (m, 12H, 4a'-, 8a'-, 12a'-, 13'-CH$_3$), 1.0–1.6 (m, 26H, 4'-, 8'-, 12'-CH, 1'-,2'-,3'-,5'-, 6'-,7'-,9'-,10'-,11'-CH$_2$, 2a-CH$_3$), 1.81 (m, 2H, 3-CH$_2$), 2.14, 2.17, 2.21 (3×s, 9H, 5a-, 7a-, 8a-CH$_3$), 2.62 (t, J=6.6 Hz, 2H, 4-CH$_2$), 2.72 (t, J=7.2 Hz, 2H, CH$_2$COOH), 3.74 (t, J=6.1 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.9 (2a-CH$_3$), 24.4, 24.8, 25.3 (CH$_2$), 28.0 (CH), 30.9, 31.2 (3-CH$_2$), 32.7, 32.8 (CH), 37.3, 37.4, 37.5, 39.4, 40.0 (CH$_2$), 71.3 (OCH$_2$), 74.8 (2-C), 117.5, 122.9. 125.7, 127.7 (aryl C), 147.8, 147.9 (aryl C—O), 178.9 (COOH); HRMS (CI, m/z): 516.424374 (M+H$^+$, Calc. for C$_{33}$H$_{57}$O$_4$ 516.424386).

2,5,7,8-Tetramethyl-2R-(4R,8R,12-trimethyltridecyl) chroman-6-yloxy)valeric Acid (4)

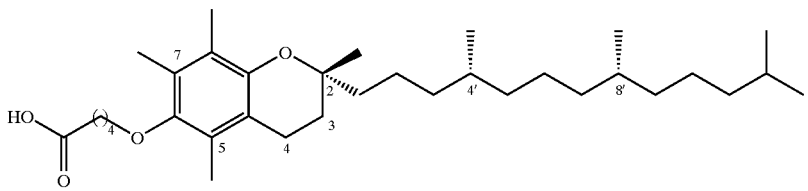

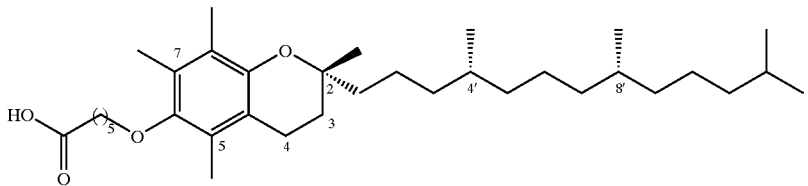

(77% yield). $^1$H-NMR (CDCl$_3$/TMS, ppm): 0.87 (m, 12H, 4a'-, 8a'-, 12a'-, 13'-CH$_3$), 1.0–1.6 (m, 30H, 4'-, 8'-,12'-CH, 1'-,2'-,3'-,6'-,7'-,9'-,10'-,11'-CH$_2$, 2a-CH$_3$), 1.81 (m, 2H, 3-CH$_2$), 2.08, 2.12, 2.16 (3xs, 9H, 5a-, 7a-, 8a-CH$_3$), 2.32 (t, J=6.5 Hz, 2H, CH$_2$COOH), 2.57 (t, J=6.6 Hz, 2H, 4-CH$_2$), 3.64 (t, J=5.5 Hz, 2H, OCH$_2$); $^{13}$C-NMR (CDCl$_3$, ppm): 11.8, 11.9, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.6, 24.8, 25.7 (CH$_2$), 28.0 (CH), 30.0 (CH$_2$), 31.3 (3-CH$_2$), 32.7, 32.8 (CH), 34.0, 37.3, 37.3, 37.4, 39.3, 40.0 (CH$_2$), 72.6 (OCH$_2$), 74.7 (2-C), 117.4, 122.7, 125.4, 127.8 (aryl C), 147.6, 148.2 (aryl C—O), 179.6 (COOH); HRMS (CI, m/z): 545.457026 (M+H$^+$, Calc. for C$_{35}$H$_{61}$O$_4$ 545.456986).

2,5,7,8-Tetramethyl-2R-(4R,8R,12-trimethyltridecyl)chroman-6-yloxy)octanoic Acid (6)

A solution of R,R,R-α-tocopherol (75 mg, 0.18 mmol) in N,N-dimethylformamide (2 mL) was treated with methyl bromoacetate (0.4 g, 2.8 mmol) and an excess of powdered NaOH (0.5 g, 12.5 mmol). The resulting yellow slurry was stirred vigorously for 24 h at room temperature. The reaction was acidified with 5 N HCl and extracted with diethyl ether (3×10 ml). The combined ether layers were washed with H$_2$O (3×10 ml) and brine (1×10 ml), and then dried with Na$_2$SO$_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H$_2$O (3×10 mL) and brine (1×10 mL), and then dried with Na$_2$SO$_4$. The resulting solution was concentrated to a light yellow oil and dried in vacuo for 48 h. This

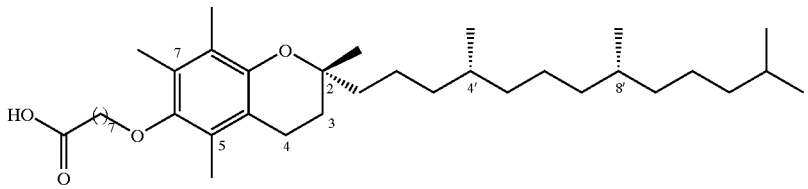

(91% yield). $^1$H-NMR (CDCl$_3$/TMS, ppm): 0.87 (m, 12H, 4a'-, 8a'-, 12a'-, 13'-CH$_3$), 1.0–1.6 (m, 34H, 4'-, 8'-,12'-CH, 1'-,2'-,3'-,5'-,6'-,7'-,9'-,10'-,11'-CH$_2$, 2a-CH$_3$), 1.81 (m, 2H, 3-CH$_2$), 2.08, 2.11, 2.16 (3xs, 9H, 5a-, 7a-, 8a-CH$_3$), 2.36 (m, 2H, CH$_2$COOH), 2.58 (t, J=6.6 Hz, 2H, 4-CH$_2$), 3.62 (t, J=5.5 Hz, 2H, OCH$_2$); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.6, 24.8, 25.1, 25.7, 26.6 (CH$_2$), 28.0 (CH), 30.0 (CH$_2$), 31.3 (3-CH$_2$), 32.7, 32.8 (CH), 34.0, 37.3, 37.3, 37.4, 39.3, 40.0 (CH$_2$), 72.7 (OCH$_2$), 74.6 (2-C), 117.6, 122.8. 125.5, 127.6 (aryl C), 147.5, 148.3 (aryl C—O), 179.4 (COOH); HRMS (CI, m/z): 573.484396 (M+H$^+$, Calc. for C$_{37}$H$_{65}$O$_4$ 573.488286).

2,5,8-Trimethyl-(2R-(4R,8R,12-trimethyltridecyl)chroman-6-yloxy)acetic Acid (7)

yielded 7 as a waxy, off-white solid (80 mg, 97%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-,12'-CH, 1'-,2'-,5'-,6'-,7'-,9'-,10'-,11'-CH$_2$, 2a-CH$_3$), 1.81 (m, 2H, 3-CH$_2$), 2.12, 2.14 (2xs, 6H, 5a-, 8a-CH$_3$), 2.61 (t, J=6.6 Hz, 2H, 4-CH$_2$), 4.59 (s, 2H, OCH), 6.53 (s, 1H, aryl CH); $^{13}$C-NMR (CDCl$_3$, ppm): 11.2, 16.1 (5a-, 8a-CH$_3$), 19.6, 19.7 (CH$_3$), 20.7, 21.0 (CH$_2$), 22.6, 22.7 (CH$_3$), 23.8 (2a-CH$_3$), 24.4, 24.8 (CH$_2$), 27.9 (CH), 31.2 (3-CH$_2$), 32.7, 32.8 (CH), 37.2, 37.4, 37.5, 39.4, 40.0 (CH$_2$), 66.8 (OCH$_2$), 74.8 (2-C), 113.8, 120.7, 123.1, 127.3 (aryl C), 147.1, 148.2 (aryl C—O), 175.3 (COOH); HRMS (CI, m/z): 475.377840 (M+H$^+$, Calc. for C$_{30}$H$_{51}$O$_4$ 475.378736).

2,7,8-Trimethyl-(2R-(4R,8R,12-trimethyltridecyl)chroman-6-yloxy)acetic Acid (8)

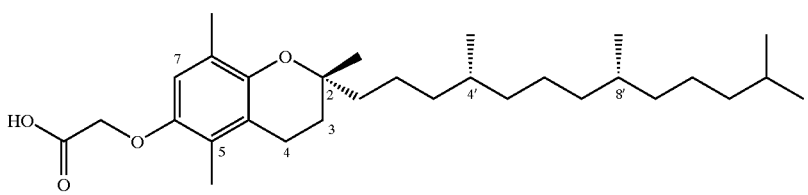

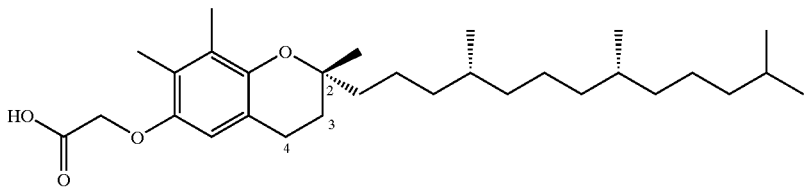

A solution of R,R,R-α-tocopherol (100 mg, 0.24 mmol) in N,N-dimethylformamide (5 mL) was treated with methyl bromoacetate (1.1 g, 7.4 mmol) and an excess of powdered NaOH (1.0 g, 25 mmol). The resulting yellow slurry was stirred vigorously for 24 h at room temperature. The reaction was acidified with 5 N HCl and extracted with diethyl ether (3×10 ml). The combined ether layers were washed with $H_2O$ (3×10 ml) and brine (1×10 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×10 mL) and brine (1×10 mL), and then dried with $Na_2SO_4$. The resulting solution was concentrated to a light yellow oil and dried in vacuo for 48 h. This yielded 8 as a waxy, off-white solid (110 mg, 97%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-, 5'-,6'-,7'-,9'-,10'-,11'-CH$_2$, 2a-CH$_3$), 1.81 (m, 2H, 3-CH$_2$), 2.12, 2.19 (2×s, 6H, 7a-, 8a-CH$_3$), 2.61 (t, J=6.6 Hz, 2H, 4-CH$_2$), 4.59 (s, 2H, OCH$_2$), 6.39 (s, 1H, aryl CH); $^{13}$C-NMR (CDCl$_3$, ppm): 11.9, 12.0 (7a-, 8a-CH$_3$), 19.6, 19.7 (CH$_3$), 20.7, 21.0 (CH$_2$), 22.6, 22.7 (CH$_3$), 23.8 (2a-CH$_3$), 24.4, 24.8 (CH$_2$), 27.9 (CH), 31.2 (3-CH$_2$), 32.7, 32.8 (CH), 37.2, 37.4, 37.5, 39.4, 40.0 (CH$_2$), 66.6 (OCH$_2$), 75.7 (2-C), 110.6, 117.7, 125.0, 126.3 (aryl C), 146.9, 148.7 (aryl C—O), 175.0 (COOH); HRMS (CI, m/z): 475.377962 (M+H$^+$, Calc. for C$_{30}$H$_{51}$O$_4$ 475.378736).

2,8-Dimethyl-(2R-(4R,8R,12-trimethyltridecyl)chroman-6-yloxy)acetic Acid (9 bromoacetate (1.1 g, 7.4 mmol) and an excess of powdered NaOH (1.0 g, 25 mmol). The resulting yellow slurry was stirred vigorously for 24 h at room temperature. The reaction was acidified with 5 N HCl and extracted with diethyl ether (3×10 ml). The combined ether layers were washed with $H_2O$ (3×10 ml) and brine (1×10 ml), and then dried with $Na_2SO_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with $H_2O$ (3×10 mL) and brine (1×10 mL), and then dried with $Na_2SO_4$. The resulting solution was concentrated to a light yellow oil and dried in vacuo for 48 h. This yielded 9 as a waxy, off-white solid (111 mg, 98%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-, 5'-,6'-,7'-,9'-,10'-,11'-CH$_2$, 2a-CH$_3$), 1.81 (m, 2H, 3-CH$_2$), 2.15 (s, 3H, 8a-CH$_3$), 2.71 (t, J=6.6 Hz, 2H, 4-CH$_2$), 4.59 (s, 2H, OCH$_2$), 6.48 (d, J=3.0 Hz, 1H, aryl CH), 6.61 (d, J=3.0 Hz, 1H, aryl CH); $^{13}$C-NMR (CDCl$_3$, ppm): 16.2 (8a-CH$_3$), 19.6, 19.7 (CH$_3$), 21.0 (CH$_2$), 22.6, 22.7 (CH$_3$), 24.0 (2a-CH$_3$), 24.4, 24.8 (CH$_2$), 27.9 (CH), 31.2 (3-CH$_2$), 32.7, 32.8 (CH), 37.2, 37.4, 37.5, 39.4, 40.0 (CH$_2$), 65.7 (OCH$_2$), 75.8 (2-C), 112.3, 115.6, 121.1, 127.5 (aryl C), 147.2, 149.9 (aryl C—O), 174.8 (COOH); HRMS (CI, m/z): 460.3552022 (M+H$^+$, Calc. for C$_{30}$H$_{51}$O$_4$ 460.355262).

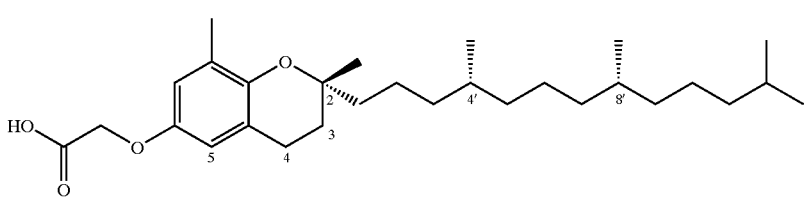

A solution of R,R,R-α-tocopherol (100 mg, 0.25 mmol) in N,N-dimethylformamide (5 mL) was treated with methyl 2,5,7,8-Tetramethyl-(2R-(4R,8R,12-trimethyltridecyl)chroman-6-yloxy)acetamide (10)

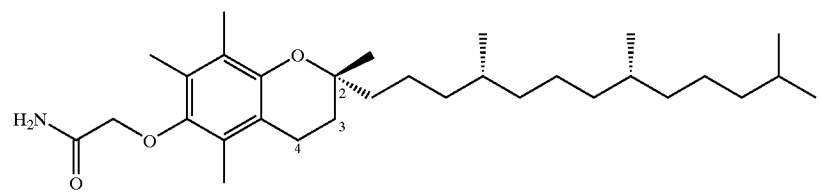

A solution of 1 (0.1 g, 0.2 mmol) in $CH_2Cl_2$ (5 mL) was treated with N-hydroxysuccinimide (26 mg, 0.23 mmol) and dicyclohexylcarbodiimide (46 mg, 0.23 mmol). After 2 min, a white precipitate formed. The resulting suspension was stirred for 2 h. The reaction stirred for an additional 6 h. The reaction mixture was cooled to −30° C. and filtered. The filtrate was concentrated and the resulting colorless oil was purified by silica gel chromatography eluting with EtOAc (35%, v/v) in hexanes. This yielded a white solid (75 mg, 76%). $^1$H-NMR ($CDCl_3$/TMS, ppm): 0.87 (m, 12H, 4a'-, 8a'-, 12a'-, 13'-$CH_3$), 1.0-1.6 (m, 24H, 4'-, 8'-, 12'-CH, 1'-,2'-,3'-,5'-,6'-,7'-,9'-,10'-,11'-$CH_2$, 2a-$CH_3$), 1.81 (m, 2H, 3-$CH_2$), 2.10, 2.12, 2.16 (3×s, 9H, 5a-, 7a-, 8a-$CH_3$), 2.59 (t, J=6.6 Hz, 2H, 4-$CH_2$), 4.19 (s, 2H, $OCH_2$), 6.36, 6.92 (2×broad, 2H, NH); $^{13}$C-NMR ($CDCl_3$, ppm): 11.7, 11.8, 12.7 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 70.9 ($OCH_2$), 74.9 (2-C), 117.8, 123.3. 125.4, 127.3 (aryl C), 146.5, 148.4 (aryl C—O), 172.1 (COOH); HRMS (CI, m/z): 488.409341 (M+H$^+$, Calc. for $C_{31}H_{54}NO_3$ 488.410370).

Methyl2,5,7,8-tetramethyl-(2R-(4R,8R,12-trimethyltridecyl)chroman-6-yloxy)acetate (11)

A solution of 1 (0.2 g, 0.4 mmol) in $CH_2Cl_2$ (5 mL) was treated with diethyl iminodiacetate (77 mg, 0.4mmol) and O-7-azabenzotriazol-1-yl-N,N,N',N'-tetramethyuronium hexafluorophosphate (HATU) (46 mg, 0.23 mmol). After 12 h, the reaction mixture was concentrated to a paste and then purified by silica gel chromatography eluting with EtOAc (30%, v/v) in hexanes. This yielded the desired diester intermediate as colorless oil (150 mg, 55%). $^1$H-NMR ($CDCl_3$/TMS, ppm): 0.87 (m, 12H, 4a'-, 8a'-, 12a'-, 13'-$CH_3$), 1.0–1.6 (m, 30H, 4'-, 8'-,12'-CH, 1'-,2'-,3'-,5'-,6'-,7'-, 9'-,10'-11'-$CH_2$, 2a-$CH_3$), 1.78 (m, 2H, 3-$CH_2$), 2.08, 2.13, 2.17 (3×s, 9H, 5a-, 7a-, 8a-$CH_3$), 2.58 (t, J=6.8 Hz, 2H, 4-$CH_2$), 4.19, 4.22 (q, J=7.4 Hz, 4H, $OCH_2$), 4.30, 4.33, 4.42 (3×s, 6H, 2×$NCH_2$, $OCH_2$); $^{13}$C-NMR ($CDCl_3$, ppm): 11.7, 11.8, 12.7 (5a-, 7a-, 8a-$CH_3$), 14.0 ($CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 48.1, 49.4 ($NCH_2$), 61.2, 61.5 $OCH_2$), 71.8 ($OCH_2$), 74.8 (2-C), 117.5, 122.9. 125.6, 127.4 (aryl C), 148.0, 148.1 (aryl C—O), 168.8, 169.0 (CO); MS (CI, m/z): 660 (M+H$^+$, Calc. for $C_{39}H_{65}NO_7$ 659.47610).

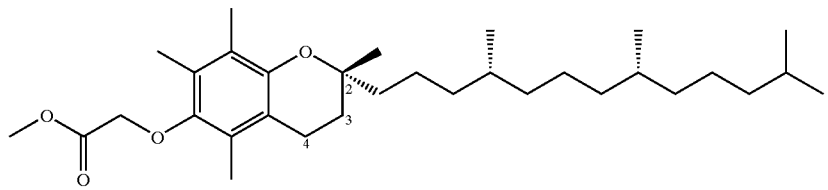

A solution of 1 (0.1 g, 0.2 mmol) in $CH_2Cl_2$ (5 mL) was treated with N,N-dimethylaminopyridine (26 mg, 0.23 mmol), methanol (1 ml) and dicyclohexylcarbodiimide (46 mg, 0.23 mmol) After 2 min, a white precipitate formed. The resulting suspension was stirred for 6 h. The reaction mixture was cooled to −30° C. and filtered. The filtrate was concentrated and the resulting colorless oil was purified by silica gel chromatography eluting with EtOAc (40%, v/v) in hexanes. This yielded a white solid (82 mg, 80%). $^1$H-NMR ($CDCl_3$/TMS, ppm): 0.87 (m, 12H, 4a'-, 8a'-, 12a'-, 13'-$CH_3$), 1.0–1.6 (m, 24H, 4'-, 8'-,12'-CH, 1'-,2'-,3'-,5'-,6'-,7'-, 9'-,10'-,11'-$CH_2$, 2a-$CH_3$), 1.81 (m, 2H, 3-$CH_2$), 2.10, 2.16, 2.20 (3×s, 9H, 5a-, 7a-, 8a-$CH_3$), 2.59 (t, J=6.6 Hz, 2H, 4-$CH_2$), 3.85 (s, 3H, $OCH_3$), 4.32 (s, 2H, $OCH_2$); $^{13}$C-NMR ($CDCl_3$, ppm): 11.7, 11.8, 12.7 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 50.2 ($OCH_3$), 69.8 ($OCH_2$), 74.9 (2-C), 117.6, 123.0, 125.6, 127.5 (aryl C), 147.6, 148.2 (aryl C—O), 169.8 (COOH); HRMS (CI, m/z): 503.408411 (M+H$^+$, Calc. for $C_{32}H_{55}O_4$ 503.410036).

2-(N,N-(Carboxymethyl)-2(2,5,7,8-tetramethyl-(2R-(4R,8R,12-trimethyltridecyl)chroman-6-yloxy)acetic Acid (12)

A solution of the diester intermediate (0.15 g, 0.23 mmol) in ethanol (4 ml) was treated with 1 N NaOH (1 ml). The resulting cloudy mixture was stirred at 70° C. for 15 h. The reaction mixture was acidified with 1 N HCl and the ethanol was removed in vacuo. The resulting aqueous solution was extracted with $CHCl_3$ (5×20 ml) and the combined organic layers dried with $Na_2SO_4$. This yielded 12 (0.13 g, 52%) as a white solid. $^1$H-NMR ($CDCl_3$/TMS, ppm): 0.87 (m, 12H, 4a'-, 8 a'-, 12a'-, 13'-$CH_3$), 1.0–1.6 (m, 24H, 4'-, 8'-, 12'-CH, 1'-, 2'-,3'-,5'-,6'-, 7'-,9'-,10'-,11'-$CH_2$, 2a-$CH_3$), 1.70 (m, 2H, 3-$CH_2$), 2.01, 2.05, 2.08 (3×s, 9H, 5a-, 7a-, 8a-$CH_3$), 2.47 (m, 2H, 4-$CH_2$), 4.18 (m, 4H, 2×$NCH_2$), 4.31 (m, 2H, $OCH_2$); $^{13}$C-NMR ($CDCl_3$, ppm): 11.5, 11.6, 12.4 (5a-, 7a-, 8a-$CH_3$), 19.4, 19.5 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.4, 32.5 (CH), 37.0, 37.2, 37.5, 39.1, 40.0 ($CH_2$), 48.1, 49.4 ($NCH_2$), 71.1 ($OCH_2$), 74.8 (2-C), 117.5, 122.9. 125.4, 127.2 (aryl C), 147.8, 148.1 (aryl C—O), 168.8, 169.0 (CO); HRMS (CI, m/z): 604.420882 (M+H$^+$, Calc. for $C_{35}H_{58}NO_7$ 604.421329).

2-(2,5,7,8-Tetramethyl-(2R-(4R,8R,12-trimethyltridecyl)chroman-6-yloxy))ethan-1-ol (13)

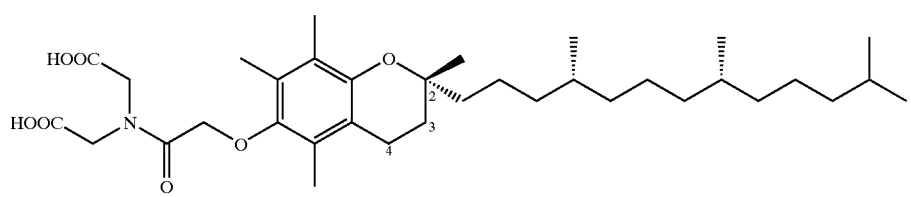

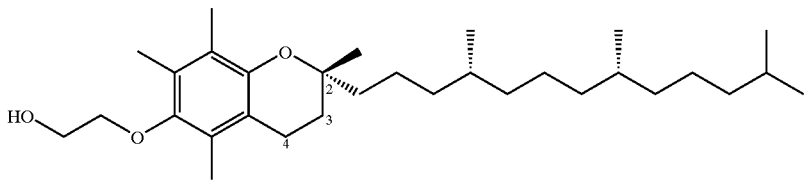

A solution of R,R,R-α-tocopherol (0.5 g, 1.16 mmol) in N,N-dimethylformamide (20 mL) was treated with iodoethanol (1.7 g, 1 0 mmol) and an excess of powdered NaOH (2.5 g, 63 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 13 as yellow oil (0.40 g, 73%). $^1$H-NMR (CDCl$_3$/TMS, ppm): 0.87 (m, 12H, 4a'-, 8a'-, 12a'-, 13'-CH$_3$), 1.0-1.6 (m, 24H, 4'-, 8'-, 12'-CH, 1'-,2'-,3'-,5'-,6'-,7'-,9'-,10'-,11'-CH$_2$, 2a-CH$_3$), 1.81 (m, 2H, 3-CH$_2$), 2.07, 2.14, 2.16 (3×s, 9H, 5a-, 7a-, 8a-CH$_3$), 2.59 (t, J=6.6 Hz, 2H, 4-CH$_2$), 3.79 (m, 2H, OCH$_2$), 3.94 (m, 2H, OCH); $^{13}$C-NMR (CDCl$_3$, ppm): 11.7, 11.8, 12.7 (5a-, 7a-, 8a-CH$_3$), 19.6, 19.7 (CH$_3$), 20.6, 21.0 (CH$_2$), 22.6, 22.7 (CH$_3$), 23.8 (2a-CH$_3$), 24.4, 24.8 (CH$_2$), 28.0 (CH), 31.2 (3-CH$_2$), 32.7, 32.8 (CH), 37.3, 37.4, 37.5, 39.4, 40.0 (CH$_2$), 63.1, 69.2 (OCH$_2$), 75.0 (2-C), 117.8, 123.4, 126.4, 128.3 (aryl C), 149.2, 149.5 (aryl C—O); MS (CI, m/z): 475 (M+H$^+$, Calc. for C$_{31}$H$_{54}$O$_3$ 474.40729).

2-(2,5,7,8-Pentamethylchroman-6-yloxy)acetic Acid (14)

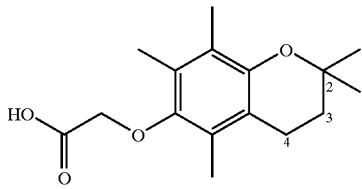

A solution of 2,2,5,7,8-pentamethyl-6-chromanol (0.3 g, 1.36 mmol) in N,N-dimethylformamide (20 mL) was treated with methyl bromoacetate (0.8 g, 5.3 mmol) and an excess of powdered NaOH (0.7 g, 18 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 14 as a white solid (0.31 g, 82%). $^1$H-NMR (CDCl$_3$/TMS, ppm): 1.31 (s, 6H, CH$_3$), 1.81 (t, J=7.8 Hz, 3-CH$_2$), 2.10, 2.16, 2.19 (3×s, 9H, 5a-, 7a-, 8a-CH$_3$), 2.61 (t, J=7.8 Hz, 2H, 4-CH$_2$), 4.39 (s, 2H, OCH$_2$); $^{13}$C-NMR (CDCl$_3$, ppm): 11.7, 11.8, 12.7 (5a-, 7a-, 8a-CH$_3$), 20.9, 26.8, 32.7 (alkyl), 69.1, (OCH$_2$), 72.9 (2-C), 117.5, 123.2, 125.5, 127.3 (aryl), 147.0, 148.6 (O-aryl), 173.8 (COOH); HRMS (CI, m/z): 279.159238 (M+H$^+$, Calc. for C$_{16}$H$_{23}$O$_4$ 279.159634).

2,5,7,8-Tetramethyl-(2RS-(4RS,8RS,12-trimethyltridecyl) chroman-6-yloxy)acetic Acid (15)

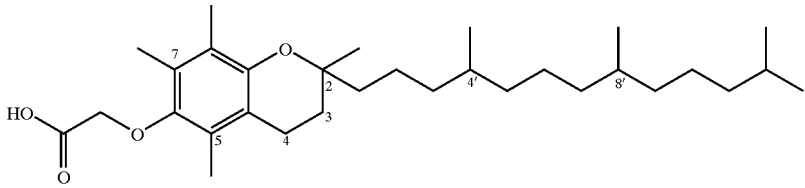

A solution of all racemic-α-tocopherol (0.5 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml),and then dried with Na$_2$SO$_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 15 as a waxy, off-white solid (80%). $^1$H-NMR (CDCl$_3$/TMS, ppm): 0.88 (m, 12H, 4a'-, 8a'-, 12a'-, 13'-CH$_3$), 1.0–1.6 (m, 24H, 4'-, 8'-,12'-CH, 1'-, 2'-,3'-,5'-,6'-, 7'-,9'-,10'-,11'-CH$_2$, 2a-CH$_3$), 1.84 (m, 2H, 3-CH$_2$), 2.07, 2.14, 2.16 (3×s, 9H, 5a-, 7a-, 8a-CH$_3$), 2.61 (t, J=6.6 Hz, 2H, 4-CH$_2$), 4.34 (s, 2H, OCH$_2$); $^{13}$C-NMR (CDCl$_3$, ppm): 11.5, 11.7, 12.6 (5a-, 7a-, 8a-CH$_3$), 19.6, 19.7 (CH$_3$), 20.6, 21.3 (CH$_2$), 22.6, 22.8 (CH$_3$), 23.8 (2a-CH$_3$), 24.5, 24.9 (CH$_2$), 29.0 (CH), 31.6 (3-CH$_2$), 32.6, 32.8 (CH), 37.5, 37.8, 37.9, 39.5, 41.0 (CH$_2$), 69.3 (OCH$_2$), 75.1 (2-C), 117.9, 123.3, 125.5, 127.3 (aryl C), 147.0, 148.0 (aryl C—O), 173.9 (COOH); HRMS (CI, m/z): 489.394375 (M+H$^+$, Calc. for C$_{31}$H$_{53}$O$_4$ 489.394383).

2,5,7,8-Tetramethyl-(2R-(carboxy)chroman-6-yloxy))acetic Acid (16)

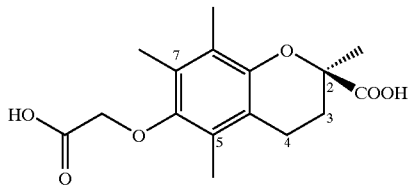

A solution of (−)-(R)-6-hydroxy-2,5,7,8-tetramethylchroman-2-carboxylic acid (0.34 g, 1.36 mmol) in N,N-dimethylformamide (20 mL) was treated with methyl bromoacetate (0.8 g, 5.3 mmol) and an excess of powdered NaOH (0.7 g, 18 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 30% (v/v) EtOAc and 2% acetic acid in hexanes. The resulting yellow liquid was dissolved in diethyl ether (30 ml), washed with $H_2O$ (3×20 mL) and brine (1×20 mL), and then dried with $Na_2SO_4$. The resulting solution was concentrated to light yellow oil and dried in vacuo for 48h. This yielded 16 as a white solid (0.33 g, 80%). $^1$H-NMR (CDCl$_3$/TMS, ppm): 1.52 (s, 3H, 2a-CH$_3$), 2.10 (m, 2H, 3-CH$_2$), 2.12, 2.16, 2.19 (3×s, 9H, 5a-, 7a-, 8a-CH$_3$), 2.56 (t, J=6.5 Hz, 2H, 4-CH$_2$), 4.36 (s, 2H, OCH$_2$).

2,5,7,8-Tetramethyl-2R-(2RS,6RS,10-trimethylundecyl)chroman-6-yloxy)acetic Acid (17)

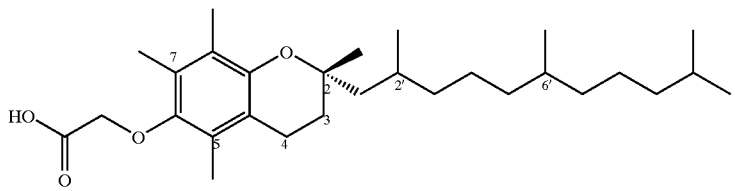

A solution of 10 g (40 mmol) of (−)-(S)-6-hydroxy-2,5,7,8-tetramethylchroman-2-carboxylic acid and 0.5 g of p-toluenesulfonic acid monohydrate in 200 ml of methanol was stirred and refluxed for 4 hr. After cooling, the solution was diluted with water and extracted with diethyl ether. The combined ether layers were washed with saturated aqueous sodium bicarbonate solution, $H_2O$, and brine (1×30 ml), and then dried with $Na_2SO_4$. The resulting solution was concentrated and dried in vacuo for 48 h. This yielded 10 g (95%) of methyl (−)-(S)-6-hydroxy-2,5,7,8-tetramethylchroman-2-carboxylate as a colorless solid which was used without further purification. $^1$H-NMR (CDCl$_3$/TMS, ppm): 1.52 (s, 3H, 2a-CH$_3$), 2.10 (m, 2H, 3-CH$_2$), 2.12, 2.16, 2.19 (3×s, 9H, 5a-, 7a-, 8a-CH$_3$), 2.56 (t, J=6.5 Hz, 2H, 4-CH$_2$), 3.55 (s, 3H, OCH$_3$); MS (CI, m/z): 264.422 M+H$^+$, Calc. for $C_{15}H_{20}O_4$ 265.3224.

To a solution of 2 g (7.58 mmol) of this ester in 7.5ml of N,N-dimethylformamide (DMF) was added 2.6 g (18.8 mmol) of anhydrous granular potassium carbonate followed by 2.3 ml (20 mmol) of benzylchloride. The resulting slurry was stirred at RT for 41 h then poured into 50 ml of water and worked up with ether in the usual way. The product was freed of excess benzyl chloride at 500 under high vacuum.

There was obtained 2.69 g (100%) of pure (TLC) (−)-(S)-6-benzyloxy-2,5,7,8-tetramethyl-chroman-2carboxylic acid methyl ester as a yellow solid, m.p. 102–106°. The analytical specimen of this compound was prepared as a colorless solid m.p. 108–109° (from ether/methanol). $^1$H-NMR (CDCl$_3$/TMS, ppm): 1.54 (s, 3H, 2a-CH$_3$), 2.01 (m, 2H, 3-CH$_2$), 2.14, 2.17, 2.19 (3×s, 9H, 5a-, 7a-, 8a-CH$_3$), 2.51 (t, J=6.7 Hz, 2H, 4-CH$_2$), 3.64 (s, 3H, OCH$_3$), 5.12(s, 2H, 6-OCH$_2$), 7.15 (m,5H, ArH); MS (CI, m/z): 355.232 M+H$^+$, Calc. for $C_{22}H_{25}O_4$ 354.448.

A solution of 3.54 g (10 mmol) of the above ether ester, in 20 ml of toluene and 10 ml of $CH_2Cl_2$ was stirred with cooling from dry ice/acetone bath while 12 ml (18 mmol) of 25% disobutylaluminum hydride in toluene (Texas Alkyls) was added dropwise, over 10 min. After stirring at ca. −70° for 30 min, the reaction mixture was cautiously decomposed (−70°) with 10 ml of MeOH. Following the addition of 50 ml of water and 50 ml of 1N aqueous $H_2SO_4$ solution, the mixture was warmed to RT, and worked up with ether in the usual way giving 3.2 g (100%) of crude aldehyde [(+)S-6-Benzyloxy-2,5,7,8-tetramethylchroman-2-carbaldehyde] as a viscous oil which was purified by silica gel chromatography eluting with 19% (v/v) EtOAc in hexane. $^1$H-NMR (CDCl$_3$/TMS, ppm): 1.53 (s, 3H, 2a-CH$_3$), 2.11 (m, 2H, 3-CH$_2$), 2.24, 2.27, 2.29 (3×s, 9H, 5a-, 7a-, 8a-CH$_3$), 2.481 (t, J=6.7 Hz, 2H, 4-CH$_2$), 5.19(s, 2H, 6-OCH$_2$), 7.20 (m,5H, ArH), 9.6(s,1H, CHO); MS (CI, m/z): 325.332 M+H$^+$, Calc. for $C_{21}H_{24}O_3$ 324.422.

A solution of 9.6 g of pseudoionone was dissolved in 100 ml of 95% ethanol; after 0.68 g of sodium borohydride in ethanol had been added at room temperature, the mixture was stirred for 2 hr and then left standing overnight. The mixture was added to a solution of 2 g of sodium hydroxide in 500 ml of water. The mixture was extracted with ether, and the ether extract was washed with water, dried, and concentrated. The distillation of the residual oil in vacuo gave a colorless oil (pseudoionol); bp 112–120° C./5 mmHG. 7.7 g (80%).

To a solution of 2.97 g of pseudoionol in 10 ml of acetonitrile, there were added, under stirring and while the temperature was kept below 30° C., 4.53 g of triphenylphospine hydrochloride which had been obtained by passing dry hydrogen chloride into a solution of triphenylphosphine in dry ether. After the mixture had been left standing overnight at room temperature, the acetonitrile was removed under reduced pressure below 50° C. To the residue there were added 4.47 gm of (+)S-6-Benzyloxy-2,5,7,8-tetramethylchroman-2-carbaldhyde in 15 ml of dimethylformamide, and the mixture was stirred. When a clear solution was obtained, sodium methoxide prepared from 0.352 g of sodium and 7 ml of anhydrous methanol was stirred in, drop by drop below 15° C. The reaction mixture was turned red by the ylid formed. After the addition was complete, stirring was continued for 30 min at 10° C.; then the mixture was gradually heated to 80° C., when the red color disappeared. The product was poured into 200 ml of 50% aqueous methanol, dried, and concentrated in vacuo.

The residual oil was dissolved in 20 ml of ether, and an etheral solution of mercuric chloride was added until no more precipitate formed. When the precipitate was filtered and the filtrate was washed with water, dried and concentrated, to give 4.7 g of yellow oil were obtained. The crude mixture of cis and trans alkene (MS (CI, m/z): 485.22, M+H$^+$, Calc. for $C_{34}H_{44}O_2$ 484.7255) was dissolved in 30 ml of ethyl acetate and 0.80 g of 5% palladium on carbon was added, and the mixture was shaken under 40 psi of $H_2$ for 30 hrs and then filtered through Celilte and rinsed well with ethyl acetate. The filtrate was concentrated and purified by silica gel chromatography eluting with EtOAc in hexane (1:9) to give 2,5,7,8-tetramethyl-(2R-(2RS,6RS,10-trimethylundecyl))-6-chromanol (60% yield) $^1$H-NMR (CDCl$_3$/TMS, ppm): 0.97 (m, 12H, 2a'-, 6a'-, 10a'-, 11'-CH$_3$), 1.1–1.7 (m, 20H, 2'-, 6'-,10'-CH, 1'-,3'-4'-,5'-,7'-,8'-, 9'-CH$_2$, 2a-CH$_3$), 1.88 (m, 2H, 3-CH$_2$), 2.17, 2.19, 2.20 (3×s, 9H, 5a-, 7a-, 8a-CH$_3$), 2.63 (t, J=6.7 Hz, 2H, 4-CH$_2$); (MS (CI, m/z): 403.27, M+H$^+$, Calc. for $C_{27}H_{46}O_2$ 402.6632.

A solution of 2,5,7,8-tetramethyl-(2R-(2RS,6RS,10-trimethylundecyl))-6-chromanol (0.466 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. This yielded compound 17 in 76% yield. $^1$H-NMR (CDCl$_3$/TMS, ppm): 0.97 (m, 12H, 2a'-, 6a'-, 10a'-, 11'-CH$_3$), 1.2–1.7 (m, 20H, 2'-, 6'-,10'-CH, 1'-,3'-4'-,5'-,7'-,8'-,9'-CH$_2$, 2a-CH$_3$), 1.92 (m, 2H, 3-CH$_2$), 2.18, 2.20, 2.23 (3×s, 9H, 5a-, 7a-, 8a-CH$_3$), 2.68 (t, J=6.8 Hz, 2H, 4-CH$_2$), 4.48 (s, 2H, OCH$_2$); MS (CI, m/z): 461.44, M+H$^+$, Calc. for $C_{29}H_{48}O_4$ 460.700. 2,5,7,8-Tetramethyl-2R-(2,6,10-trimethyl-1,3,5,9E:Zdecatetraen)chroman-6-yloxy)acetic Acid (18)

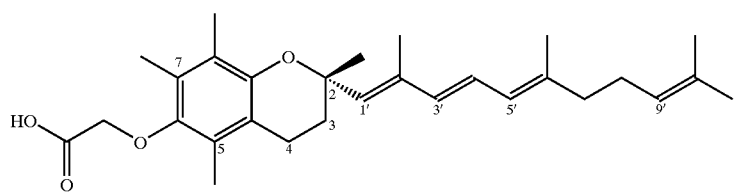

To a solution of methyl (−)-(S)-6-hydroxy-2,5,7,8-tetramethylchroman-2-carboxylate (20 gms 0.075 mole) in 50 ml of dry DMF, imidazole (13 gm, 0.1911 mole), and tert-butyldimethyl-silylchloride (14 gm, 0.0933 mole) were added. The mixture was stirred at 23° C. for 24 hr and then treated with ether and poured into 1N HCl. The organic extracts were dried (brine, Na$_2$SO$_4$) and concentrated in vacuo. The crude product was purified by flash chromatography (9:1 hexane:ethyl acetate) to yield 6-[dimethyl(1,1-dimethylethyl)silyl]-2,5,7,8-tetramethyl-chroman-2-carboxylate (TBS protected methyl ester). $^1$H-NMR (CDCl$_3$/TMS, ppm): 0.12(s, 6H). 1.102(s, 9H), 1.18 (s, 3H), 1.48 (s, 3H), 1.645 (s, 3H), 2.07(s, 3H), 2.2 (t, J=6.5hz 2H), 2.48–2.7 (m, 2H) and 3.72(s,3H, OCH$_3$) (MS (CI, m/z): 379.32, M+H$^+$, Calc. for $C_{21}H_{34}O_4$ 378.586.

A solution of 3.78 g(10 mmol) of the above ether ester, in 20 ml of toluene and 10 ml of CH$_2$Cl$_2$ was stirred with cooling from dry ice/acetone bath while 12 ml (18 mmol) of 25% disobutylaluminum hydride in toluene (Texas Alkyls) was added dropwise, over 10 min. After stirring at ca. −70° was added for 30 min, the reaction mixture was cautiously decomposed (−70°) with 10 ml of MeOH. Following the addition of 50 ml of water and 50 ml of 1N aqueous H$_2$SO$_4$ solution, the mixture was warmed to RT, and worked up with ether in the usual way giving 3.2 g (90%) of crude aldehyde [(+)S-6-[dimethyl(1,1-dimethylethyl)silyl]-2,5,7,8-tetramethyl-chroman-2-carbaldhyde] as a viscous oil which was purified by silica gel chromatography eluting with 19% (v/v) EtOAc in hexane. Concentration of the solution followed by drying under vacuo for 48 h yielded TBDS aldehyde (78%) as a solid of mp 66–68° C. $^1$H-NMR (CDCl$_3$/TMS, ppm): 0.12(s, 6H). 1.1(s, 9H), 1.38 (s, 3H), 1.64 (s, 3H), 2.12 (s, 3H), 2.16(s, 3H), 2.3–2.2 (m, 2H), 2.53 (m, 2H) and 9.82(d, J=1.4Hz, 1H); MS (CI, m/z): 349.40 M+H$^+$, Calc. for $C_{20}H_{32}SiO_3$ 348.560.

To a solution of 2.97 g of psedoionol in 10 ml of acetonitrile, there were added, under stirring and while the temperature was kept below 30° C., 4.53 g of triphenylphospine hydrochloride which had been obtained by passing dry hydrogen chloride into a solution of triphenylphosphine in dry ether. After the mixture had then been left standing overnight at room temperature, the acetonitrile was removed under reduced pressure below 50° C. To the residue there were added 4.80 gm of [(+)S-6-[dimethyl(1,1-dimethylethyl)silyl]-2,5,7,8-tetramethylchroman-2-carbaldhyde] in 15 ml of dimethylformamide, and the mixture was stirred. When a clear solution was obtained, sodium methoxide prepared from 0.352 g of sodium and 7 ml of anhydrous methanol was stirred in, drop by drop below 15° C. The reaction mixture was turned red by the ylid formed. After the addition was complete, stirring was continued for 30 min at 10° C.; then the mixture was gradually heated to 80° C., when the red color disappeared. The product was poured into 200 ml of 50% aqueous methanol, dried, and concentrated in vacuo. The residual oil was dissolved in 20 ml of ether, and an etheral solution of mercuric chloride was added until no more precipitate formed. When the precipitate was filtered and the filtrate was washed with water, dried and concentrated, to give 4.7 g of yellow oil were obtained. The crude silyl ether mixture of cis and trans alkene was dissolved in THF and tetra-n-butylammoniumfluoride (0.031 mole) was added. After being stirred at 23° C. for 40 minutes, the mixture was poured into water and extracted into ether. The ether extract was dried concentrated and purified by silica gel chromatography eluting with EtOAc in hexane (1:9) to give 2,5,7,8-tetramethyl-2R-(2,6,10-trimethyl-1,3,5,9E:Zdecatetraen)-6-chromanol (68% yield). $^1$H-NMR (CDCl$_3$/TMS, ppm): 1.28 (s, 3H, 2aCH$_3$), 1.65(s, 3H), 1.70(s,6H) 1.72 (s,3H), 1.9(m, 6H), 2.18 (s,3H), 2.35 (S, 6H), 2.53 (t, J=6.6Hz, 2H, 4CH$_2$), 5.13–5.27 (m, 3H) and 6.44(m, 2H) ; MS (CI, m/z): 395.17 M+H$^+$, Calc. for $C_{27}H_{38}O_2$ 394.60.

A solution of 2,5,7,8-tetramethyl-2R-(2,6,10-trimethyl-1,3,5,9E:Zdecatetraen)-6-chromanol (0.457 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with $H_2O$ (3×20 mL) and brine (1×20 mL), and then dried with $Na_2SO_4$. The resulting solution was concentrated and dried in vacuo for 48 h. This yielded compound 18 in 67% yield. $^1$H-NMR ($CDCl_3$/TMS, ppm): 1.24 (s, 3H, 2a$CH_3$), 1.63(s, 3H), 1.72(s,6H) 1.74 (s,3H), 1.92(m, 6H), 2.18 (s,3H), 2.29 (S, 6H), 2.43 (t, J=6.6Hz, 2H, 4$CH_2$), 4.68 (s,2H, $OCH_2$), 5.10–5.27 (m, 3H) and 6.34(m, 2H); MS (CI, m/z): 452.24 M-H$^+$, Calc. for $C_{27}H_{38}O_2$ 452.63.

3-(2,5,7,8-Tetramethyl-(2R-(4R,8,12-trimethyltridecyl) chroman-6-yloxy)propyl-1-ammonium Chloride (19)

solution was concentrated to a yellow oil that was purified by silica gel chromatography eluting with EtOAc (10% v/v) in hexanes. This yielded desired ether as a colorless oil (0.45 g, 66%). $^1$H-NMR ($CDCl_3$/TMS, ppm): 0.87 (m, 12H, 4a'-, 8a'-, 12a'-, 13'-$CH_3$), 1.0–1.6 (m, 33H, 4'-, 8'-, 12'-CH, 1'-, 2'-,3'-, 5'-,6'-,7'-,9'-,10'-,11'-$CH_2$, 2a-$CH_3$), 1.81 (m, 2H, 3-$CH_2$), 1.99 (quintet, J=6.2 Hz, 2H, $CH_2$), 2.07, 2.14, 2.16 (3×s, 9H, 5a-, 7a-, 8a-$CH_3$), 2.59 (t, J=6.6 Hz, 2H, 4-$CH_2$), 3.43 (m, 2H. N$CH_2$), 3.73 (t, J=5.7 Hz, 2H, $OCH_2$), 4.34 (s, 2H, $OCH_2$); $^{13}$C-NMR ($CDCl_3$, ppm): 11.7, 12.0, 12.9 (5a-, 7a-, 8a-$CH_3$), 19.6, 19.7 ($CH_3$), 20.6, 21.0 ($CH_2$), 22.6, 22.7 ($CH_3$), 23.7 (2a-$CH_3$), 24.4, 24.8 ($CH_2$), 27.9 (CH), 31.2 (3-$CH_2$), 32.7, 32.8 (CH), 37.2, 37.4, 37.5, 39.3, 40.1 ($CH_2$), 70.2 ($OCH_2$), 74.8 (2-C), 117.5, 122.9, 125.5, 127.5 (aryl C), 147.5, 148.0 (aryl C—O), 156.0 (CO); MS (CI, m/z): 589 M+H$^+$, Calc. for $C_{37}H_{65}NO_4$ 587.49136.

The above N-protected ether (0,1 g, 0.17 mmol) was dissolved 4 N HCl in dioxane (1 mL, 4 mmol) and stirred for 4 h. The dioxane was removed by blowing a stream of argon over the reaction mixture. The resulting material was dried in vacuo for 8 h yielding 19 as a white solid (82 mg, 99%).

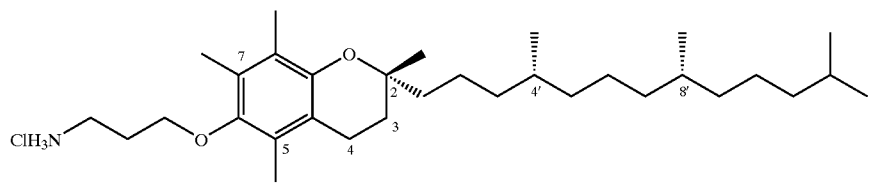

A solution of 3-bromopropylamine hydrobromide (1.0 g, 4.6 mmol) in a 2:1 dioxane/$H_2O$ (45 mL) was cooled to 0° C. and treated with $K_2CO_3$ (6.22 g, 45 mmol) and di-tert-butyl dicarbonate (1.5 g, 6.9 mmol). The reaction was stirred for 15 h while warming to room temperature. The dioxane was removed in vacuo and the remaining aqueous mixture was acidified with 5 N HCl and extracted with ethyl acetate (5×25 mL). The combined organic layers were dried with $MgSO_4$ and yielded 3-bromo-N-(tert-butoxycarbonyl) propylamine as a colorless oil (0.93 g, 93%). $^1$H-NMR ($CDCl_3$/TMS, ppm): 1.41 (s 9H, $CH_3$), 2.02 (quintet, J=6.4 Hz, 2H, $CH_2$), 3.23 (m, 2H, N$CH_2$), 3.41 (t, J=6.6 Hz, $CH_2$Br), 4.8 (broad, 1H, NH); $^{13}$C-NMR ($CDCl_3$, ppm): 28.3 ($CH_3$), 30.7, 32.6, 38.9 ($CH_2$), 79.3 (quaternary C), 155.9 (CO); MS (CI, m/z): 239, 241 (M+H$^+$ Calc. for $C_8H_{16}BrNO_2$ 237.03644).

A solution of R,R,R-α-tocopherol (0.5 g, 1.16 mmol) in N,N-dimethylformamide (15 mL) was treated with 3-bromo-N-(tert-butoxycarbonyl)propylamine (0.9 g, 3.8 mmol) and an excess of powdered NaOH (0.32 g, 8 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether $^1$H-NMR ($CDCl_3$/TMS, ppm): 0.87 (m, 12H, 4a'-, 8a'-, 12a'-, 13'-$CH_3$), 1.0–1.6 (m, 33H, 4'-, 8'-, 12'-CH, 1'-,2'-,3'-, 5'-,6'-,7'-,9'-,10'-,11'-$CH_2$, 2a-$CH_3$), 1.81 (m, 2H, 3-$CH_2$), 1.99 (quintet, J=6.2 Hz, 2H, $CH_2$), 2.07, 2.11, 2.15 (3×s, 9H, 5a-, 7a-, 8a-$CH_3$), 2.29 (m, 2H, $CH_2$), 2.59 (t, J=6.6 Hz, 2H, 4-$CH_2$), 3.43 (m, 2H. N$CH_2$), 3.79 (m, 2H, $OCH_2$) $^{13}$C-NMR ($CDCl_3$, ppm): 11.8, 11.9, 12.7 (5a-, 7a-, 8a-$CH_3$), 19.6, 19.7 ($CH_3$), 20.6, 21.0 ($CH_2$), 22.6, 22.7 ($CH_3$), 23.9 (2a-$CH_3$), 24.4, 24.8 ($CH_2$), 28.0 (CH), 28.4 ($CH_3$), 31.2 (3-$CH_2$), 32.7, 32.8 (CH), 37.3, 37.4, 37.5, 39.4, 40.0 ($CH_2$), 74.8 ($OCH_2$), 75.0 (2-C), 117.5, 122.9, 126.0, 127.3 (aryl C), 147.8, 148.0 (aryl C—O); HRMS (CI, m/z): 487.438887 (M+H$^+$, Calc. for $C_{32}H_{57}NO_2$ 487.438935).

2,5,7,8-Tetramethyl-(2R-(4R,8R,12-trimethyltridecyl) chroman-3-ene-6-yloxy)acetic Acid (20)

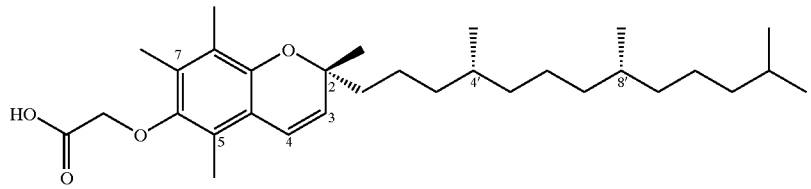

A solution of R,R,R,-α-tocopherol acetate (2 g, 4.2 mmol) in anhydrous toluene (150 mL) was heated to reflux and then treated with 2,3-dichloro-5,6-dicyano-1,4-benzoquinone (0.96 g, 4.2 mmol) in 4 portions at 1 h intervals. The reaction was refluxed for 24 h. During this time the reaction mixture became a dark red color and then it precipitated a light colored solid. The reaction was cooled to room temperature, filtered, and the filtrate was concentrated. The resulting dark colored oil was purified by silica gel chromatography eluting with ethyl acetate (10%, v/v) in hexanes. This yielded the desired chromene acetate as a colorless oil (1.74 g, 88%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-, 5'-,6'-,7'-,9'-,10'-,11'-CH$_2$, 2a-CH$_3$), 2.07, 2.13, 2.18 (3xs, 9H, 5a-, 7a-, 8a-CH$_3$), 2.35 (s, 3H, CH$_3$CO—), 5.61, 6.52 (2xd, J=10.0 Hz, 2H, CH); $^{13}$C-NMR (CDCl$_3$, ppm): 11.5, 11.6, 13.1 (5a-, 7a-, 8a-CH$_3$), 14.1 (CH$_3$), 19.6, 19.7 (CH$_3$), 20.4, 21.4 (CH$_2$), 22.6, 22.7 (CH$_3$), 24.4, 24.8 (CH$_2$), 25.8 (2a-CH$_3$), 27.9 (CH), 30.8 (3-CH$_2$), 32.7, 32.8 (CH), 37.2, 37.4, 39.4, 41.0 (CH$_2$), 60.3 (2-C), 117.6, 119.7, 122.3, 122.6, 128.9, 129.6 (aryl and vinyl C), 141.2, 148.4 (aryl C—O), 169.4 (CO); HRMS (CI, m/z): 471.375799 M+H$^+$, Calc. for C$_{31}$H$_{50}$O$_3$ 470.375996.

A solution of the chromene acetate (1.0 g, 2.13 mmol) in ethanol (20 mL) was treated with 2 N NaOH (20 mL) and stirred at 60° C. for 90 min. The reaction mixture was cooled, acidified with 5 N HCl, and the ethanol was removed in vacuo. The resulting aqueous solution was extracted with ether and concentrated to a light yellow oil that was purified by silica gel chromatography eluting with ethyl acetate (15%, v/v) in hexanes. This yielded the desired chromene-6-ol intermediate as a colorless oil (0.92 g, 98%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-, 5'-,6'-, 7'-,9'-,10'-,11'-CH$_2$, 2a-CH$_3$), 2.14, 2.18, 2.19 (3xs, 9H, 5a-, 7a-, 8a-CH$_3$), 5.63, 6.55 (2xd, J=10.0 Hz, 2H, CH); $^{13}$C-NMR (CDCl$_3$, ppm): 10.8, 11.6, 12.4 (5a-, 7a-, 8a-CH$_3$), 19.6, 19.7 (CH$_3$), 21.3 (CH$_2$), 22.6, 22.7 (CH$_3$), 24.4, 24.8 (CH$_2$), 25.2 (2a-CH$_3$), 27.9 (CH), 30.9 (3-CH$_2$), 32.7, 32.8 (CH), 37.2, 37.4, 37.5, 39.3, 40.5 (CH$_2$), 50.8 (2-C), 116.2, 117.8, 120.1, 122.3, 123.0, 130.0 (aryl and vinyl C), 144.6, 145.3 (aryl C—O), 169.4 (CO); HRMS (CI, m/z): 428.365275 M+H$^+$, Calc. for C$_{29}$H$_{48}$O$_2$ 428.365431.

A solution of the chromene-6-ol intermediate (0.9 g, 2.1 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with H$_2$O (3×30 ml) and brine (1×30 ml), and then dried with Na$_2$SO$_4$. The ether solution was concentrated to a yellow oil that was purified by silica gel chromatography eluting with 19% (v/v) EtOAc and 2% acetic acid in hexanes. The resulting yellow liquid was dissolved in diethyl ether (30 ml), washed with H$_2$O (3×20 mL) and brine (1×20 mL), and then dried with Na$_2$SO$_4$. The resulting solution was concentrated to a light yellow oil and dried in vacuo for 48 h. This yielded 19 as a colorless (0.90 g, 88%). $^1$H-NMR (CDCl$_3$/TMS, ppm): 0.87 (m, 12H, 4a'-, 8a'-, 12a'-, 13'-CH$_3$), 1.0–1.6 (m, 24H, 4'-, 8'-, 12'-CH, 1'-,2'-,3'-, 5'-,6'-,7'-,9'-,10'-,11'-CH$_2$, 2a-CH$_3$), 2.07, 2.10, 2.19 (3xs, 9H, 5a-, 7a-, 8a-CH$_3$), 4.37 (s, 2H, OCH$_2$), 5.62, 6.50 (2xd, J=10.0 Hz, 2H, CH); $^{13}$C-NMR (CDCl$_3$, ppm): 11.3, 11.5, 12.9 (5a-, 7a-, 8a-CH$_3$), 19.6, 19.7 (CH$_3$), 21.3 (CH$_2$), 22.6, 22.7 (CH$_3$), 24.4, 24.8 (CH$_2$), 25.6 (2a-CH$_3$), 27.9 (CH), 30.9 (3-CH$_2$), 32.7, 32.8 (CH), 37.2, 37.4, 37.5, 39.3, 40.9 (CH$_2$), 60.5 (OCH$_2$), 69.1 (2-C), 118.0, 119.8, 122.8, 122.9, 129.6, 19.8 (aryl and vinyl C), 147.5, 147.8 (aryl C—O), 173.4 (CO); HRMS (CI, m/z): 487.378731 M+H$^+$, Calc. for C$_{31}$H$_{51}$O$_4$ 487.378736.

2-(2,5,7,8-Tetramethyl-(2R-(4R,8,12-trimethyltridecyl) chroman-6-yloxy)triethylammonium Sulfate (21)

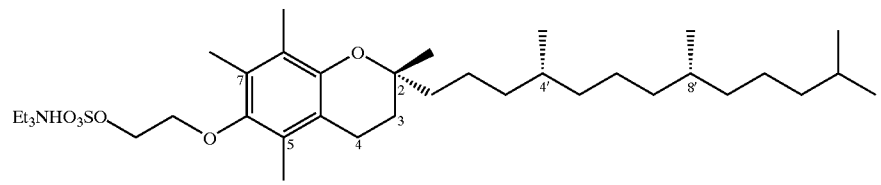

A solution of 2-(2,5,7,8-tetramethyl-(2R-(4R,8R,12-trimethyltridecyl)chroman-6-yloxy))ethan-1-ol (13) (0.1 g, 0.21 mmol) in anhydrous DMF (2 mL) and pyridine (0.6 mL) was treated sulfur trioxide-N,N-dimethylformamide complex (0.16 g, 1.0 mmol), and the resulting solution was stirred for 24 h. The reaction mixture was quenched with 1 N HCl and then extracted with CH$_2$Cl$_2$ (5×5 mL). Gaseous ammonia was bubbled through the CH$_2$Cl$_2$ solution for 10 min. The resulting solution was concentrated to a yellow paste and purified by silica gel chromatography eluting with MeOH (10%, v/v) and triethyl amine (2%) in CHCl$_3$. This yielded 21 as a yellow semi-solid (92 mg, 77%) $^1$H-NMR (CDCl$_3$/TMS, ppm): 0.87 (m, 12H, 4a'-, 8a'-, 12a'-, 13'-CH$_3$), 1.0-1.6 (m, 33H, 4'-, 8'-,12'-CH, 1'-, 2'-,3'-,5'-,6'-,7'-, 9'-,10'-,11'-CH$_2$, 2a-CH$_3$), 1.81 (m, 2H, 3-CH$_2$), 1.95 2.01, 2.05 (3xs, 9H, 5a-, 7a-, 8a-CH$_3$), 2.45 (t, J=6.6 Hz, 2H, 4-CH$_2$), 3.05 (m, 6H, NCH$_2$), 3.79 (m, 2H, OCH$_2$), 4.21 (m, 2H, OCH$_2$); $^{13}$C-NMR (CDCl$_3$, ppm): 9.46 (CH$_3$), 12.4, 12.6, 13.5 (5a-, 7a-, 8a-CH$_3$), 20.3, 20.4 (CH$_3$), 21.3, 21.7 (CH$_2$), 23.3, 23.4 (CH$_3$), 24.5 (2a-CH$_3$), 25.1, 25.5 (CH$_2$), 28.6 (CH), 31.9 (3-CH$_2$), 33.3, 33.4 (CH), 37.9, 38.1, 40.0, 40.8 (CH$_2$), 46.9 (NCH$_2$), 67.4, 71.9 (OCH$_2$), 75.5 (2-C), 118.3, 123.5, 126.5, 128.3 (aryl C), 148.5 (aryl C—O); HRMS (CI, m/z): 554.364102 M–NH$_3$, Calc. for C$_{31}$H$_{54}$O$_6$S 554.364119.

6-(2,5,7,8-Tetramethyl-(2R-(4R,8,12-trimethyltridecyl) chroman)acetic Acid (22)

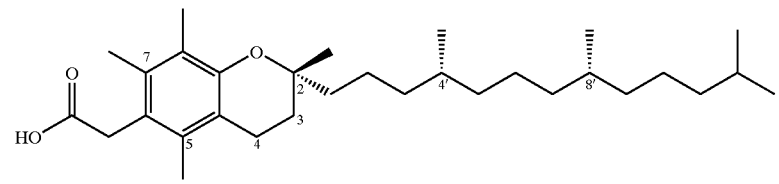

A solution of R,R,R-α-tocopherol (1.0 g, 2.3 mmol) in anhydrous CH$_2$Cl$_2$ (25 mL) was cooled to 0° C. Diisopropylethyl amine (2 mL, 11.6 mmol) was added followed by the dropwise addition of trifluoromethylsulfonic anhydride (5.0 g, 17.7 mmol). The solution turned to a dark immediately and was allowed to warm to room temperature while stirring for 24 h. The reaction was quenched with $H_2O$ and then was extracted with diethyl ether (2×100 mL). The combined ether layers were washed with 1 N HCl (50 mL), $H_2O$ (50 mL), brine (50 mL), and then dried with $MgSO_4$. The ether solution was concentrated to a yellow oil and purified by silica gel chromatography eluting with ethyl acetate (3%, v/v) in hexane. This yielded the desired triflate intermediate as a yellow oil (1.3 g, quantitative). $^1$H-NMR ($CDCl_3$/TMS, ppm): 0.87 (m, 12H, 4a'-, 8a'-, 12a'-, 13'-$CH_3$), 1.0–1.6 (m, 24H, 4'-, 8'-, 12'-CH, 1'-, 2'-,3'-,5'-,6'-,7'-, 9'-,10'-,11'-$CH_2$, 2a-$CH_3$), 1.81 (m, 2H, 3-$CH_2$), 2.07, 2.13, 2.21 (3×s, 9H, 5a-, 7a-, 8a-$CH_3$), 2.62 (t, J=6.6 Hz, 2H, 4-$CH_2$); $^{13}$C-NMR ($CDCl_3$, ppm): 11.9, 13.2, 14.0 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 75.6 (2-C), 118.4, 124.4, 126.7, 128.1 (aryl C), 139.6, 150.9 (aryl C—O); $^{19}$F-NMR ($CDCl_3$, ppm): −73.52; HRMS (CI, m/z): 563.337803 ($M+H^+$, Calc. for $C_{30}H_{50}O_4F_3S$ 563.338192).

A solution of the triflate (1.3 g, 2.31 mmol) in anhydrous DMF (23 mL) was treated with LiCl (0.98 g, 4.62 mmol), triphenylphosphine (0.37 g, 1.4 mmol), 2,6-di-tert-butyl-4-methylphenol (2–3 crystals), tributyl(vinyl)tin (0.73 g, 2.31 mmol), and dichlorobis(triphenylphosphine)-palladium (II) (0.24 g, 0.35 mmol). This mixture was heated to 120° C. and stirred. After 2 h, additional tributyl(vinyl)tin (0.73 g, 2.31 mmol). After 8 h, the reaction was cooled to room temperature and added to a mixture of $H_2O$ (50 mL) and diethyl ether (50 mL). The ether layer was washed with 1 N HCl (6×30 mL) and a saturated solution of KF (6×30 mL). The ether solution was dried with $Na_2SO_4$ and then concentrated to a dark oil. This material was purified by silica gel chromatography eluting with ethyl acetate (3%, v/v) in hexane yielding the 6-vinylchroman intermediate as a clear oil (0.38 g, 38%). $^1$H-NMR ($CDCl_3$/TMS, ppm): 0.87 (m, 12H, 4a'-, 8a'-, 12a'-, 113'-$CH_3$), 1.0–1.6 (m, 24H, 4'-, 8'-, 12'-CH, 1'-,2'-,3'-,5'-,6-,7'-,9'-,10'-, 11'-$CH_2$, 2a-$CH_3$), 1.86 (m, 2H, 3-$CH_2$), 2.20, 2.24, 2.28 (3×s, 9H, 5a-, 7a-, 8a-$CH_3$), 2.62 (t, J=6.8 Hz, 2H, 4-$CH_2$), 5.18, 5.56 (2×dd, $J_{gem}$=2.3 Hz, $J_{cis}$=11.2 Hz, $J_{trans}$=18.7 Hz, 2H,=$CH_2$), 6.77 (dd, J=18.7, 11.2 Hz, 1H, CH); $^{13}$C-NMR ($CDCl_3$, ppm): 11.9, 16.3, 17.2 (5a-, 7a-, 8a-$CH_3$), 19.7, 19.8 ($CH_3$), 20.8, 21.1 ($CH_2$), 22.6, 22.7 ($CH_3$), 23.9 (2a-$CH_3$), 24.5, 24.8 ($CH_2$), 28.0 (CH), 31.2 (3-$CH_2$), 32.7, 32.8 (CH), 37.3, 37.5, 37.5, 39.4, 40.1 ($CH_2$), 74.9 (2-C), 116.7, 119.0, 122.0, 129.8, 131.2, 132.8, 136.8 (aryl/vinyl C), 150.9 (aryl C—O); HRMS (CI, m/z): 440.401602 ($M+H^+$, Calc. for $C_{31}H_{52}O$ 440.401812).

A solution of the 6-vinylchroman intermediate (0.12 g, 0.27 mmol) in anhydrous THF (1 mL) was cooled to 0° C. and treated with 9-BBN (0.60 mL, 0.5 M in THF, 0.3 mmol). The reaction mixture was heated to reflux for 8 h. The reaction was quenched with water (1.5 mL) and treated with $NaBO_3 \cdot 4H_2O$ and the resulting slurry was stirred overnight. Diethyl ether (4 mL) and the reaction mixture were extracted with $CH_2Cl_2$ (2×20 mL). The organic layers were concentrated to a clear oil that was purified by silica gel chromatography eluting with ethyl acetate (50%, v/v) in hexane. This yielded the desired 6-(2-hydroxyethyl)chroman intermediate as a colorless oil (30 mg, 24%). $^1$H-NMR ($CDCl_3$/TMS, ppm): 0.87 (m, 12H, 4a'-, 8a'-, 12a'-, 13'-$CH_3$), 1.0–1.6 (m, 24H, 4'-, 8'-, 12'-CH, 1'-,2'-,3'-,5'-,6'-,7'-, 9'-, 10'-,11'-$CH_2$, 2a-$CH_3$), 1.81 (m, 2H, 3-$CH_2$), 2.17, 2.24, 2.28 (3×s, 9H, 5a-, 7a-, 8a-$CH_3$), 2.68 (t, J=6.8 Hz, 2H, 4-$CH_2$), 3.01 (t, J=7.5 Hz, 2H, Ar—$CH_2$), 3.74 (t, J=7.5 Hz, 2H, $OCH_2$); $^{13}$C-NMR ($CDCl_3$, ppm): 12.0, 15.1, 16.0 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 31.2 (3-$CH_2$), 32.7, 32.8 (CH), 37.3, 37.4, 37.5, 39.4, 40.0 ($CH_2$), 62.2 ($OCH_2$), 72.6 (2-C), 116.8, 122.3, 124.9, 132.4, 133.9 (aryl C), 150.1 (aryl C—O); HRMS (CI, m/z): 458.412154 ($m+H^+$, Cal. for $C_{31}H_{54}O_2$ 458.412384).

A solution of pyridinium chlorochromate (32 mg, 0.1 mmol) in anhydrous $CH_2Cl_2$ (0.5 mL) was treated with a solution of the 6-(2-hydroxyethyl)chroman intermediate (32 mg, 0.07 mmol) in $CH_2Cl_2$ (0.5 mL). The reaction was stirred for 2 h at which time no starting material was visible by thin layer chromatography. Diethyl ether (2 mL) was added and the resulting solution was filtered through a thin pad of celite. The filtrate as concentrated and yielded a yellow oil (20 mg). This oil was dissolved in t-BuOH (0.5 mL) and treated with phosphate buffer (0.5 mL, 1 N, pH=4.0), 2-methyl-2-butene (0.1 mL) and $NaClO_2$ (5.4 mg, 0.05 mmol). After stirring for 40 min, the reaction mixture was extracted with $CHCl_3$ (6×10 mL) and the combined organic layers were dried with $Na_2SO_4$. The $CHCl_3$ solution was concentrated to a yellow oil that was purified by preparative thin layer chromatography eluting with ethyl acetate (30%, v/v) and acetic acid (1%) in hexanes. This yielded 22 as colorless oil (20 mg, 63%). $^1$H-NMR ($CDCl_3$/TMS, ppm): 0.87 (m, 12H, 4a'-, 8a'-, 12a'-, 13'-$CH_3$), 1.0–1.6 (m, 24H, 4'-, 8'-, 12'-CH, 1'-,2'-,3'-,5'-, 6'-,7'-,9'-, 10'-,11'-$CH_2$, 2a-$CH_3$), 1.81 (m, 2H, 3-$CH_2$), 2.17, 2.24, 2.28 (3×s, 9H, 5a-, 7a-, 8a-$CH_3$), 2.66 (t, J=6.8 Hz, 2H, 4-$CH_2$), 3.71 (s, 2H, $CH_2COOH$); $^{13}$C-NMR ($CDCl_3$, ppm): 12.0, 15.3, 16.2 (5a-, 7a-, 8a-$CH_3$), 19.6, 19.7 ($CH_3$), 20.6, 21.0 ($CH_2$), 22.6, 22.7 ($CH_3$), 23.8 (2a-$CH_3$), 24.4, 24.8 ($CH_2$), 28.0 (CH), 28.9, 31.2 (3-$CH_2$), 32.7, 32.8 (CH), 37.3, 37.4, 37.5, 39.4, 40.0 ($CH_2$), 72.6 (2-C), 117.1, 122.2, 124.9, 132.4, 132.7 (aryl C), 150.2 (aryl C—O), 179.2 (COOH); HRMS (CI, m/z): 472.391583 ($M+H^+$, Calc. for $C_{31}H_{52}O_3$ 472.391644).

2,5,7,8-Tetramethyl-(2R-(heptyl)chroman-6-yloxy)acetic Acid (23)

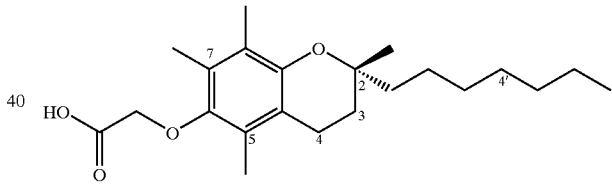

A solution of hexyltriphenyphosphonium bromide (0.880 g, 2.05 mmol) in 11.2 ml of anhydrous DME was stirred at room temperature while 0.86 ml (2.06 mmol) of 2.4 M n-butyllithium in hexane was added. The resulting red solution was stirred for 2 h at room temperature, then a solution of [(+)S-6-Benzyloxy-2,5,7,8-tetramethylchroman-2-carbaldehyde (306 mg, 0.944 mmol) in 3 ml of anhydrous DME was added and stirring was continued for 3 h at 65–75° C. After cooling, the reaction mixture was poured into cold dilute $H_2SO_4$ and work up ether was carried out in the usual manner. The ether was concentrated in vacuo to afford the oily material. Product was isolated using column chromatography and eluted with chloroform to yield 46% of the product. The mixture of cis and trans alkene was dissolved in 30 ml of ethyl acetate and 50 mg of 5% palladium on carbon was added, and the mixture was shaken under 40 psi of $H_2$ for 10 hrs and then filtered through Celilte and rinsed well with ethyl acetate. The filtrate was concentrated and purified by silica gel chromatography eluting with EtOAc in hexane (1:9) to give (2R) 2,5,7,8-tetramethyl-2-(heptyl)-6-chromanol (60% yield) $^1$H-NMR ($CDCl_3$/TMS, ppm):0.89 (s, 3H), 1.3–1.5 (m, 15H), 1.89 (m, 2H), 2.2 (s, 3H), 2.08(s, 3H), 2.23 (s, 3H), and 2.48 (t, J=6.5 Hz, 2H); MS (CI, m/z):305.35 $M+H^+$, Calc. for $C_{20}H_{32}O_2$ 304.4746).

A solution of 2,5,7,8-tetramethyl-2-(heptyl)chromanol (0.353 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with $H_2O$ (3×20 mL) and brine (1×20 mL), and then dried with $Na_2SO_4$. The resulting solution was concentrated and dried in vacuo for 48 h. This yielded compound 23 in 36% yield. $^1$H-NMR (CDCl$_3$/TMS, ppm): $^1$H-NMR (CDCl$_3$/TMS, ppm): 0.88 (s, 3H), 1.2–1.5 (m, 15H), 1.88 (m, 2H), 2.1 (s, 3H), 2.18(s, 3H), 2.2 (s, 3H), 2.55 (t, J=6.5 Hz, 2H) and 4.78 (s, 2H); HRMS (CI, m/z):363.2535 (M+H$^+$, Calc. for $C_{22}H_{35}O_4$ 363.2541).

2,5,7,8-Tetramethyl-(2R-(tridecyl)chroman-6-yloxy)acetic Acid (24)

The compounds 24 and 25 were synthesized in manner identical to the synthesis of 23 using appropriate phosphonium bromide.

3H), 2.55 (t, J=6.4 Hz, 2H), and 4.78 (s, 2H); MS (CI, m/z): 503.45 M+H$^+$, Calc. For $C_{32}H_{54}O_4$ 502.781.

2,5,7,8-Tetramethyl-2R-(4,8,-dimethyl-1,3,7E:Znonotrien) chroman-6-yloxy)acetic Acid (26)

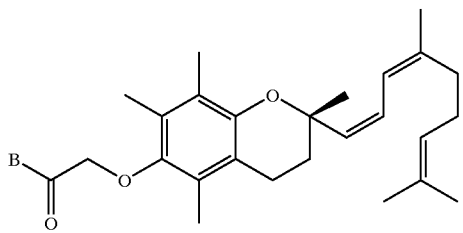

Compound 26 was synthesized in a manner identical to the synthesis of compound 18 using nerol instead of psedoionol. $^1$H-NMR (CDCl$_3$/TMS, ppm) : 1.24 (s, 3H, 2aCH$_3$), 1.63(m, 1H), 1.68 (s,3H), 1.74(s,6H), 1.92(m, 6H), 2.18 (s,3H), 2.29 (S, 6H), 2.43 (t, J=6.6Hz, 2H 4CH$_2$), 4.68 (s, 2H, OCH$_2$), 5.64(m, 2H) and 5.27 (m, 1H); MS (CI, m/z): 413.24 M+H$^+$, Calc. for $C_{26}H_{36}O_4$ 412.0115.

EZ, RS, RS, RS-(Phytyltrimethylbenzenethiol-6-yloxy) acetic Acid (27)

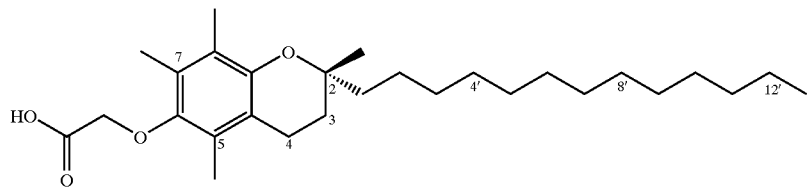

$^1$H-NMR (CDCl$_3$/TMS, ppm): 0.83 (s, 3H), 1.25–1.57 (m, 27H), 1.88 (m, 2H), 2.1 (s, 3H), 2.18 (s, 3H), 2.20(s, 3H), 2.55 (t, J=6.6 Hz, 2H) and 4.48 (s, 2H) ; MS (CI, m/z): 447.14 M+H$^+$, Calc. For $C_{28}H_{46}O_4$ 446.6732.

2,5,7,8-Tetramethyl-(2R-(heptadecyl)chroman-6-yloxy) acetic Acid (25)

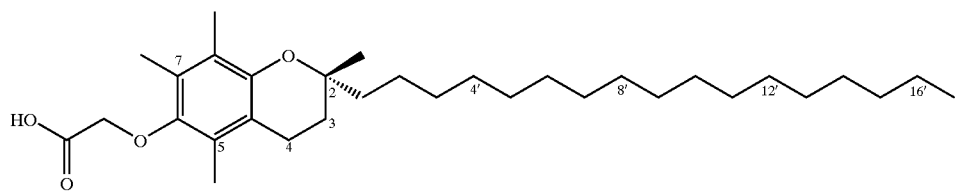

$^1$H-NMR (CDCl$_3$/TMS, ppm): 0.86 (s, 3H), 1.15–1.67 (m, 35H), 1.88 (m, 2H), 2.16 (s, 3H), 2.20 (s, 3H), 2.23(s,

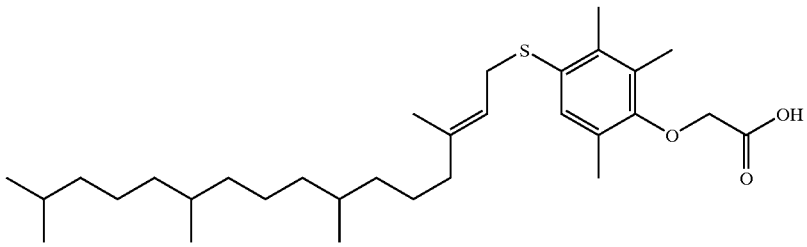

2,3,6-trimethylphenol (1.6 g, 11.8 mmol) was disolved in 50 mL of anhydrous methanol which had been deoxygenated by bubbling with nitrogen. Ammonium thiocyanate (2.2 g, 28,9 mmol) was added to this solution which was then cooled to 0° C. and bubbled with chlorine gas. The initially colorless homogeneous solution becomes pink and then green with the formation of a white precipitate. The solution was stirred for 1 h at 0° C. and then for a further hour at 20° C. The dissolved chlorine was removed by bubbling with nitrogen and the precipitate removed by filtration. Evaporation of the filtrate under reduced pressure followed by drying under high vacuum (0.1 torr) yielded 2.20 g (97%) of 2,3,5-Trimethyl-4-hydroxyphenylthiocyanate in a form pure enough for the next step in the synthesis. An analytical sample was recrystallized from hexanes : white crystals, mp 100.3° C. $^1$H NMR (CDCl$_3$) δ 7.2 (s, 1 H), 5.0 (s, 1 H) 2.4 (s, 3 H), 2.2 (s, 6 H).

2,3,5-Trimethyl-4-hydroxyphenylthiocyanate (2 g, 10.35 mmol) was dissolved in 100 mL of anhydrous ether containing 25 mL of anhydrous tetrahydrofuran. This solution was added dropwise over 1 h to 100 mL of anhydrous ether containing LiAlH$_4$ (0.9 g, 24 mmol) at room temperature. After a further hour at 20° C., the unreacted LiAlH$_4$ was destroyed by cooling the heterogeneous mixture to 0° C. and adding moist ether (50 mL), H$_2$O (50 mL), and 1 N HCl (50 mL). A further 50 mL of water was added and the organic phase was separated and washed with water (2×50 mL), NaHCO$_3$ solution (2×50 mL), water (2×50 mL), and saturated NaCl (50 mL). The organic phase was dried over anhydrous MgSO$_4$ and filtered and the solvent removed under reduced pressure. Silica gel column chromatography with 5% ethyl acetate in hexane gave 1.8 g (90%) of 2,3,5-trimethyl-4-hydroxybenzenethiol as a white powder, mp 86° C. [Lit. $^1$mp 86° C.].

Solution of 2,3,5-trimethyl-4-hydroxybenzenethiol (3 g, 17.83 mmol ), isophytol (4.8 g, 16.19 mmol), anhydrous zinc chloride (1.2 g, 8.8 mmol) and 0.2 mL of glacial acetic acid in 30 mL of absolute ether was refluxed for 1 h. The solvent was then removed in vacuo at 50° C. and the red oil obtained was dissolved in a mixture of 50 mL of petroleun ether and 20 mL of 70% aqueous methanol. The ether layer was dried (Na$_2$SO$_4$) and evaporated in vacuo to give a red oil, which was purified by silica gel chromatography eluting with hexans:ether (9:1) to give 3 g(38%) EZ, RS, RS, RS-Phytyltrimethylhydroxybenzenethiol as yellow oil. $^1$H NMR (CDCl$_3$) δ 7.11 (s, 1 H, Ar—H), 5.23 (t, 1 H, vinylic-H), 4.62 (s, 1 H, OH), 3.34 (d, 2 H, Ar—S—CH$_2$-), 2.41 (s, 3 H, Ar—CH$_3$), 2.19 (s, 3 H, Ar—CH$_3$), 2.18 (s, 3 H, Ar—CH$_3$), 0.83–1.92 (m, 39 H, Phytol chain).

A solution of phytyltrimethylhydroxybenzenethiol (3 g, 6.7 mmol) in N,N-dimethyl-formamide (80 mL) was treated with methyl bromoacetate (7.4 g, 48.3 mmol) and an excess of powdered NaOH (7 g, 175 mmol). The resulting pink oil was stirred at RT for 24 h. The reaction mixture was acidified with 5 N HCl and extracted with ether (3×150 mL). The combined ether layers were washed with H$_2$O (3×150 mL) and brine (1×150 mL), and then dried (Na$_2$SO$_4$). The ether solution was concentrated to a yellow oil that was purified by silica gel chromatography eluting with 20% EtOAc in hexane to give 3 g (88%) of EZ, RS, RS, RS-(phytyltrimethylbenzenethiol-6-yloxy)acetic acid as a yellow oil. $^1$H NMR (CDCl$_3$) δ 10.90 (s, 1 H, COOH), 8.08 (s, 1 H, Ar—H), 5.30 (t, 1 H, vinylic-H), 4.35 (s, 2 H, CH$_2$COOH), 3.42 (d, 2 H, Ar—S—CH$_2$-), 2.34 (s, 3 H, Ar—CH$_3$), 2.25 (s, 3 H, Ar—CH$_3$), 2.22 (s, 3 H, Ar—CH$_3$), 0.83–1.94 (m, 39 H, Phytyl chain). HRMS (CI, m/z): 504.362821(M+H$^+$, Calc. for C$_{31}$H$_{53}$O$_3$S 504.363718).

(R)-2[(2,5,7,8-Tetramethyl-2-(3propenemethylester) chroman-6-yloxy]acetic Acid (28)

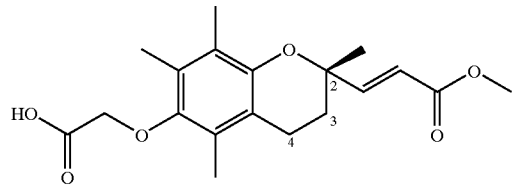

To a slurry of (carbomethoxymethyl)triphenyl phosphonium bromide (1.8 gm, 4.32 mmol) in 12 ml of THF at ° C. was added 1.66 ml of n-BuLi (2.5M in hexane) dropwise. The resulting solution was removed to room temperature for 2 h, and then a solution of (+)S-6-[dimethyl(1,1-dimethylethyl)silyl]-2,5,7,8-tetramethyl chroman-2-carbaldehyde (1.31 g, 3.76 mmol) in 7 ml THF was added via cannula. The solution was stirred at room temperature for 44 hr and then 10 ml of 1N aq. HCl was added. The layer were separated and then aq. phase was extracted with ether (3×15 ml). The combined organic layer were washed with brine, dried over Na$_2$SO$_4$ and filtered. After concentration of the filtrate, the crude alkene was purified by flash chromatography eluting with dichloromethane to give mixture of the cis and trans alkene in 93% yield. The silyl ether mixture of cis and trans alkene (3.76 mmol) was dissolved in THF and tetra-n-butylammoniumfluoride (0.041 mole) was added. After being stirred at 23° C. for 1.5 h, the mixture was poured into water and extracted into ether. The ether extract was dried concentrated and purified by silica gel chromatography eluting with EtOAc in hexane (3:7) and both the cis and trans isomer of 2,5,7,8-tetramethyl-2R-(3'propenemethyl ester)-6-chromanol were isolated and characterized (68% yield) $^1$H-NMR (CDCl$_3$/TMS, ppm): 1.65 (s, 3H, 2a CH$_3$), 2.12 (m, 2H, 3CH$_2$), 2.39 (s, 9H, CH$_3$), 2.48 (m, 2H, 4 CH$_2$), 3.78 (s, 3H, OCH$_3$), 6.11 (d, 1H, CH=) and 7.13 (d, 1H, CH=).

A solution of 2,5,7,8-tetramethyl-2R-(3'propenemethylester)6-chromanol (0.353 g, 1.16 mmol) in N,N-dimethylformamide (20 mL) was treated with methyl bromoacetate (3.4 g, 8.3 mmol) and an excess of powdered NaOH (1.2 g, 30 mmol). The resulting yellow slurry was stirred vigorously for 24 h at room temperature. The reaction was acidified with 5 N HCl and extracted with diethyl ether (3×30 ml). The combined ether layers were washed with $H_2O$ (3×30 ml) and brine (1×30 ml), and then dried with $Na_2SO_4$. The ether solution was concentrated to a yellow oil that was purified by silica gel chromatography eluting with 19% (v/v) EtOAc and 2% acetic acid in hexanes. The resulting liquid was dissolved in diethyl ether (30 ml), washed with $H_2O$ (3×20 mL) and brine (1×20 mL), and then dried with $Na_2SO_4$. The resulting solution was concentrated and dried in vacuo for 48 h. This yielded compound 28 in 40%yield. . $^1$H-NMR ($CDCl_3$/TMS, ppm): 1.68 (s, 3H, 2a $CH_3$), 2.11 (m, 2H, $3CH_2$), 2.36 (s, 9H, $CH_3$), 2.56 (m, 2H, 4 $CH_2$), 3.70 (s, 3H, $OCH_3$), 4.78 (s, 2H, $OCH_2$), 6.03 (d,1H, CH=) and 7.03 (d,1H, CH=); MS (CI, m/z):337.24 M+H$^+$, Calc. for $C_{18}H_{24}O_6$ 336.3867.

2,5,7,8-Tetramethyl-(2R-(propionate)chroman-6-yloxy) acetic Acid (29)

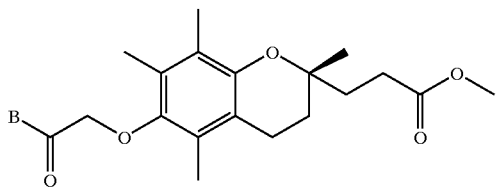

The mixture of cis and trans alkene 2,5,7,8-tetramethyl-2R-(3propenemethylester)-6-chromanol was dissolved in 30 ml of ethyl acetate and 50 mg of 5% palladium on carbon was added, and the mixture was shaken under 40 psi of $H_2$ for 24 hrs and then filtered through Celilte and rinsed well with ethyl acetate. The filtrate was concentrated and purified by silica gel chromatography eluting with EtOAc in hexane (1:9) to give compound # 29. $^1$H-NMR ($CDCl_3$/TMS, ppm): 1.62 (s, 3H, 2a $CH_3$), 2.0–2.3 (m, 6H, $CH_2$), 2.41 (s, 9H, $CH_3$), 2.53 (m, 2H, $4CH_2$), 3.67 (s, 3H, $OCH_3$) and 4.88 (s, 2H, $OCH_2$); MS (CI, m/z).339.34 M+H$^+$, Calc. for $C_{18}H_{26}O_6$ 338.4025.

EXAMPLE 3

Cell Culture Conditions

All test cell lines were cultured at 37° C. in 5% $CO_2$ in standard media supplemented with fetal calf serum, using established standard conditions. Plastic adherent cells were disassociated with trypsin, washed, counted, and used directly in experiments. All cells were examined routinely to verify no mycoplasma contamination.

EXAMPLE 4

Solubility and Dilution of Novel Tocopherol and Tocotrienol Compounds

All compounds were handled as if they were light sensitive (photodegradable). All compounds were initially dissolved in absolute ethanol and subsequently diluted to a final concentration of 0.5% ethanol with the appropriate media.

EXAMPLE 5

Determination of Effective Concentration ($EC_{50}$) to Induce Apoptosis

Whereas the parental non-structurally modified forms of tocopherols do not exhibit effective apoptotic properties against a battery of tumor cells, fifteen out of twenty-nine RRR-α-tocopherol compounds, structurally modified via ether linked moieties of different composition and size were extremely effective at inducing tumor cells to undergo apoptosis while having no apoptotic inducing properties on normal cells. Compounds 1, 2, 3, 7, 8, 9, 12, 15, 17, 19, 20, 21, 22, 25, 26, and 27 exhibit effective growth inhibitory (apoptotic inducing) properties specific for human cancer cells from a wide variety of cell lineages, including (i) breast (estrogen responsive Michigan Cancer Foundation human breast cancer cell line number 7, MCF-7 McGuire; non-estrogen responsive M. D. Anderson metastatic breast human cancer cell line, MDA-MB-435; and, estrogen non-responsive M. D. Anderson metastatic human breast cancer cell line, MDA-MB-231); (ii) prostate (androgen responsive human prostate cancer cell line, LnCaP and the androgen non-responsive human prostate cancer cell line, PC-3 and the DU-145 cell line); (iii) promyelocytic leukemia cells (human Promyelocytic Leukemia Cell Line, HL-60), lymphoid cell lines Jurkat and HL-60; (iv) cervical (human cervical cancer cell line, ME-180); (v) ovarian (human ovarian cancer cell line, C-170 cells); (vi) endometrial (human endometrial cancer cell line, RL-95-2 cells); (vii) colon cell lines DLD-1; and (viii) lung cell line A-549. Normal primary breast cells (normal primary early passage human mammary epithelial cells, HMEC) and immortalized, non-tumorigenic mammary cells (Michigan Cancer Foundation immortalized but non-tumorigenic human mammary number 10A cells, MCF-10A) do not undergo apoptosis when cultured with the above pharmacodynamically designed forms of tocopherol.

The effective therapeutic dose of novel reagents for controlling cancer growth is referred to as the growth inhibitory concentration ($IC_{50}$) or effective concentration ($EC_{50}$) that blocks 50% cancer growth via DNA synthesis inhibition, cell cycle blockage and/or cell death. The apoptotic $EC_{50}$ for a battery of test cancer cells for the twenty-nine novel compounds of this invention are presented in Tables 1 and 2.

TABLE 1

Apoptosis Induced by Novel Tocopherol Compounds ($EC_{50}$ range µg/ml)

| Cell Type | VES | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Breast Cancer | | | | | | | | | | | | | | | | |
| HMEC | N | N | N | N | N | N | N | N | N | N | N | N | N | N | N | NT |
| MCF-10A | N | N | N | N | N | N | N | N | N | N | N | N | N | N | N | NT |
| MDA-MB-435 | 5–10 | 5–10 | 10–20 | 5–10 | N | N | N | 5–10 | 5–10 | 5–10 | N | N | 5–10 | N | N | 20-30 |
| MDA-MB-231 | 5–10 | 5–10 | 10–20 | 5–10 | N | N | N | 5–10 | 5–10 | 5–10 | N | N | 5–10 | N | N | 20-30 |
| MCF-7 | 10–20 | 5–10 | 20–30 | 20–30 | N | N | N | 10–20 | 10–20 | 10–20 | N | N | 5–10 | N | N | 20–30 |
| T47D | N | N | N | N | N | N | N | N | NT | NT | NT | NT | NT | NT | NT | NT |

TABLE 1-continued

Apoptosis Induced by Novel Tocopherol Compounds (EC$_{50}$ range µg/ml)

| Cell Type | VES | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Cervical | | | | | | | | | | | | | | | | |
| ME-180 | 10–20 | 1–5 | 5–10 | 10–20 | N | N | N | 5–10 | 5–10 | 5–10 | N | N | 5–10 | N | N | N |
| Ovarian | | | | | | | | | | | | | | | | |
| C-170 | N | 10–20 | 10–20 | 10–20 | N | N | N | 10–20 | 10–20 | N | N | N | 10–20 | N | N | N |
| Endometrial | | | | | | | | | | | | | | | | |
| RL-95-2 | 10–20 | 10–20 | 10–20 | 10–20 | N | N | N | 5–10 | 1–5 | 5–10 | N | N | 5–10 | N | N | 1–5 |
| Prostate | | | | | | | | | | | | | | | | |
| PREC | N | N | NT | NT | NT | NT | NT | NT | NT | NT | NT | NT | NT | NT | NT | NT |
| LuCaP | 5–10 | 5–10 | 5–10 | 5–10 | N | N | N | 2.5–5 | 5–10 | 5–10 | N | N | >20–30 | NT | N | NT |
| PC-3 | 10–20 | 5–10 | 5–10 | 5–10 | N | N | N | 5–10 | 5–10 | 5–10 | NT | N | 10–20 | N | N | NT |
| DU-145 | 10–20 | 5–10 | NT | NT | NT | NT | NT | NT | NT | NT | NT | NT | NT | NT | NT | NT |
| Colon | | | | | | | | | | | | | | | | |
| HT-29 | 5–10 | 10–20 | NT | NT | NT | NT | NT | NT | NT | NT | NT | NT | NT | NT | NT | NT |
| DLD-1 | 10–20 | 10–20 | NT | NT | NT | NT | NT | NT | NT | NT | NT | NT | NT | NT | NT | NT |
| Lung | | | | | | | | | | | | | | | | |
| A-549 | 20–30 | 10–20 | NT | NT | NT | NT | NT | NT | NT | NT | NT | NT | NT | NT | NT | NT |
| Lymphoid Cells | | | | | | | | | | | | | | | | |
| Myeloma | 10–20 | NT | NT | NT | NT | NT | NT | NT | NT | NT | NT | NT | NT | NT | NT | NT |
| Raji | 10–20 | NT | NT | NT | NT | NT | NT | NT | NT | NT | NT | NT | NT | NT | NT | NT |
| Ramos | 10–20 | NT | NT | NT | NT | NT | NT | NT | NT | NT | NT | NT | NT | NT | NT | NT |
| Jurkat | 10–20 | 10–20 | NT | NT | NT | NT | NT | NT | NT | NT | NT | NT | NT | NT | NT | NT |
| HL-60 | 10–20 | 5–10 | 10–20 | 10–20 | N | N | N | 5–10 | 10–20 | 10–20 | N | N | 20–30 | N | N | NT |

EC$_{50}$ = µg/ml of tocopherol compounds 1–29 inducing 50% apoptosis;
N = No apoptosis when treated for 2 days with 1–60 EC$_{50}$ µg/ml of tocopherol compounds 1–29;
NT = Not tested;
* = compounds exhibiting toxicity

TABLE 2

Apoptosis Induced by Novel Tocopherol Compounds (EC$_{50}$ range µg/ml)

| Cell Type | 16 | 17 | 18 | 19 | 20 | 21 | 22 | 23 | 24 | 25 | 26 | 27 | 28 | 29 |
|---|---|---|---|---|---|---|---|---|---|---|---|---|---|---|
| Breast Cancer | | | | | | | | | | | | | | |
| HMEC | NT | NT | NT | NT | NT | NT | NT | NT | NT | NT | NT | NT | NT | NT |
| MCF-10A | NT | N | NT | N | N | N | NT | N | NT | N | N | NT | NT | NT |
| MDA-MB-435 | N | NT | N | 10–20 | 10–20 | N | NT | N | N | N | 20–40 | NT | NT | NT |
| MDA-MB-231 | N | NT | NT | NT | NT | NT | NT | NT | NT | NT | NT | NT | NT | NT |
| MCF-7 | N | 10–20 | N | 10–20 | 5–10 | N | 15–20 | N | N | N | N | 10–20 | NT | NT |
| T47D | NT | 10–20 | NT | N | 5–10* | NT | NT | NT | NT | NT | N | NT | NT | NT |
| Cervical | | | | | | | | | | | | | | |
| ME-180 | NT | 20–30 | N | 1–5 | 1–5 | 1–5 | NT | NT | NT | N | * | NT | NT | NT |
| Ovarian | | | | | | | | | | | | | | |
| C-170 | NT | 20–30 | N | 1–5 | * | N | NT | NT | NT | N | 20–30 | NT | NT | NT |
| Endometrial | | | | | | | | | | | | | | |
| RL-95-2 | NT | NT | NT | NT | NT | N | NT | NT | NT | N | 20–30 | NT | NT | NT |
| Prostate | | | | | | | | | | | | | | |
| PREC | NT | NT | N | | NT | NT | NT | NT | NT | NT | NT | NT | NT | NT |
| LuCaP | NT | 10–20 | NT | 5–10 | 5–10* | N | NT | NT | N | N | 10–20 | 10–20 | NT | NT |
| PC-3 | NT | NT | NT | N | 5–10* | N | NT | N | N | 20–30 | N | NT | NT | NT |
| DU-145 | NT | NT | NT | 5–10 | 5–10 | N | NT | N | N | 20–30 | N | NT | NT | NT |
| Colon | | | | | | | | | | | | | | |
| HT-29 | NT | N | N | NT | NT | NT | NT | N | NT | N | N | NT | NT | NT |
| DLD-1 | NT | NT | NT | NT | NT | NT | NT | NT | N | N | 20–40 | NT | NT | NT |
| Lung | | | | | | | | | | | | | | |
| A-549 | NT | N | N | 20–30 | 20–30 | NT | NT | NT | NT | NT | N | NT | NT | NT |

TABLE 2-continued

Apoptosis Induced by Novel Tocopherol Compounds (EC$_{50}$ range µg/ml)

| Cell Type | 16 | 17 | 18 | 19 | 20 | 21 | 22 | 23 | 24 | 25 | 26 | 27 | 28 | 29 |
|---|---|---|---|---|---|---|---|---|---|---|---|---|---|---|
| Lymphoid Cells | | | | | | | | | | | | | | |
| Myeloma | NT | NT | NT | NT | NT | NT | NT | NT | NT | NT | NT | NT | NT | NT |
| Raji | NT | NT | NT | NT | NT | NT | NT | NT | NT | NT | NT | NT | NT | NT |
| Ramos | NT | NT | NT | NT | NT | NT | NT | NT | NT | NT | NT | NT | NT | NT |
| Jurkat | NT | 10–20 | N | 10–20 | 10–20 | NT | NT | NT | NT | NT | 20–30 | NT | NT | NT |
| HL-60 | NT | 10–20 | N | 10–20 | 10 | NT | NT | NT | NT | NT | N | NT | NT | NT |

EC$_{50}$ = µg/ml of tocopherol compounds 1–29 inducing 50% apoptosis;
N = No apoptosis when treated for 2 days with 1–60 EC$_{50}$ µg/ml of tocopherol compounds 1–29;
NT = Not tested;
*= compounds exhibiting toxicity

EXAMPLE 6

Bioassay for Apoptosis

Cells were cultured at 1.5×10$^5$ cells/well in 12 well plates. Cells were allowed to adhere overnight, then incubated with novel test compounds at 0.01, 0.1, 1, 5, 10 & 20 _g/mL for 1, 2 and 3 days. After treatment, cells (floating+trypsin released adherent cells) were pelleted, washed and stained with 2 _g/ml DAPI (4',6-diamidine-2'-phenylindole dihydrochloride) in 100% methanol for 15 minutes at 37° C. and/or TUNEL stained, then viewed using a Zeiss ICM 405 microscope. Cells whose nucleus contained clearly condensed or fragmented chromatin were scored as apoptotic. Data are presented as percent cells undergoing apoptosis.

EXAMPLE 7

Bioassay for DNA Synthesis Arrest

To assay DNA synthesis, all cells were used at 2.5×10$^5$/ml. Cells were treated with each of the compounds 1–29 (Tables 1 and 2) at concentrations of 0.01, 0.1, 1, 5, 10 and 20 µg/mL and 200 µl of each treatment group were plated in quadruplicate in a 96 well culture plate (Corning, Corning N.Y.). Experiments were done in duplicate, one plate used for viability testing and the other plate for examination of $^3$H-TdR uptake to monitor DNA synthesis. Plates were cultured for 48 hours at 37° C., 5% CO$_2$. Eight hours prior to the end of incubation, $^3$H-TdR was added to one of the duplicate plates and incubation continued for 8 hours. The cells were then harvested (trypsinization was required to harvest adherent cells), and isotope uptake was determined as counts per minute (cpm). For viability studies, at the end of the incubation, the cells were removed from the wells and viability checked by the Trypan Blue Exclusion method. Percent viability and percent DNA synthesis in comparison to untreated or vehicle treated cells of each treatment group were calculated.

EXAMPLE 8

Bioassay for Cell Cycle Arrest

The cells were cultured with novel test agents for 2–3 days, fixed in 95% ethanol and stained with propidium iodide overnight. DNA content was determined using a Coulter Epics Elite Flow Cytometer with an argon laser setting of 488 nm. Cell size was measured simultaneously, and data were analyzed as to percent cells in each cell cycle phase using the Coulter Multicycle Program.

EXAMPLE 9

Bioassay for Cellular Differentiation

To determine if the novel compounds were inducing cellular differentiation, the cells were cultured on cover slips, fixed in 95% ethanol and stained with a lipid specific stain for detection of milk lipids. Additionally, cells were examined by immunohistology and by Western analyses for presence of milk protein casein, using polyclonal antibodies produced in the lab.

EXAMPLE 10

DNA Synthesis Arrest Effects

The cells were cultured for 48 hours, pulsed 8 hours with tritiated thymidine, harvested and counted. Data are presented as counts per minute. Verification of DNA synthesis arrest is determined by reduced tritiated thymidine uptake by cells treated with test compounds. Further verification of DNA synthesis arrest is determined by propidium iodide staining and standard cell cycle analyses.

EXAMPLE 11

Mechanisms of Induction of Apoptosis

The mechanism of induction of apoptosis by these compounds appears to involve three distinct apoptotic signaling pathways; namely, activation of latent transforming growth factor-beta (TGF-β), activation of the Fas/Fas ligand signaling pathways, and signaling by the stress kinase (c-Jun N-terminal Kinase) pathway.

TGF-βs are potent growth inhibitory molecules that are known to inhibit cell growth by inhibition of DNA synthesis arrest and by induction of apoptosis. TGF-βs are involved only in induction of the apoptotic pathway, i.e., there is no evidence curently that the TGF-βs effect DNA synthesis arrest; however, this possibility has not been completely ruled out. TGF-βs are made and secreted by cells in a latent non-active form. To be effective as tumor growth inhibitors, the latent TGF-βs must be activated by induction of cell surface proteins that provide a proper structure for processing and activating proteases that cut the latent protein and release the active TGF-β.

The compounds of the present invention are shown to activate proteases such as cathepsin D family proteases, and upregulate the mannose-6-phosphate receptor which binds inactive TGF-β and permits activation via proteases. Active TGF-_ signals via cell membrane TGF-β receptors I and II to activate down stream kinases referred to as stress kinases or c-Jun N-terminal Kinases (JNK) which phosphorylate and activate transcription factors c-Jun, ATF-2 and Elk-1. Prolonged activation of transcription factor c-Jun causes tumor cells to undergo apoptosis. These transcription factors, acting as homodimers or heterodimers with a multitude of transcription factor partners activate proapoptotic genes and/or downregulate antiapoptotic genes leading to DNA fragmentation. The compounds of the present invention do not generate an anti-proliferative outcome to TGF-β signaling in normal non-tumor cells.

A second apoptotic inducing mechanism called the Fas/Fas ligand apoptotic signaling pathway is activated by the novel compounds of the present invention. Activated Fas/Fas ligand signaling may lead to rapid cell death by apoptosis. Thus, for tumor cells to escape death by Fas/Fas ligand, they must inactivate this most important apoptotic pathway. The mechanism for inactivation of the Fas/Fas ligand signaling pathway by tumor cells varies; however, many tumor cells down regulate the expression of Fas receptor and Fas ligand on their membranes.

Most important, R,R,R-2-(2,5,7,8-tetramethyl-2-(4,8,12-trimethyltridecyl)chroman-6-yloxy)acetic acid (1) has been shown to induce Fas/Fas ligand resistant tumor cells to become Fas/Fas ligand sensitive. Compound 1 also has the ability to enhance the expression of Fas ligand on the membrane of LNCaP prostate cells. Studies show that Fas signaling resistant human breast cancer cells retain the Fas receptor in their cytoplasm, but when cultured with compound 1, the Fas receptor is transported from the cytoplasm to the membrane; thereby rendering the cells Fas signaling sensitive. Furthermore, this compound is synergistic in anti-Fas triggered apoptosis in that greater amounts of cell killing is obtained with both human breast and prostate cancer cells when co-treated versus when treated separately. The ability of compound 1 to convert Fas signaling resistant tumor cells to Fas signaling sensitive tumor cells and to exhibit synergistic killing effects provides an extremely important mechanism for destruction of tumor cells both by the host immune surveillance system as well as by pharmaceutical intervention. The compounds of the present invention do not activate the Fas signaling pathway of normal non-tumor cells.

These compounds activate the JNK kinase signaling pathway, perhaps by TGF-β and Fas/Fas ligand signaling. Prolonged activation of JNK results in prolonged activation of c-Jun and ATF-2 transcription factors, which are postulated to play a role in expression or repression of proapoptotic and antiapoptotic genes, respectively.

EXAMPLE 12

Mechanism of Induction of DNA Synthesis Arrest. Cell Cycle Arrest and Cellular Differentiation The mechanisms of growth inhibition by DNA synthesis arrest, cell cycle arrest and by induction of cellular differentiation have not been characterized as fully as the mechanism of growth inhibition by apoptosis. Studies show that the compounds of the present invention have profound effects on the cell cycle, inducing DNA synthesis arrest of approximately 95% of the tumor cells within 24 hours of treatment. Tumor cells cultured with the compounds disclosed herein are growth inhibited in the G1 cell cycle phase, undergo morphological changes and express milk lipids, an indication that the cell cycle blocked cells have undergone differentiation. P21, a gene known to be an inhibitor of entrance of cells from the G1 cell cycle phase to the S phase of the cell cycle, and the mRNA, as well as the protein of P21 gene, is up-regulated by treatment of MDA-MB-435 human breast cancer cells with compound 1.

EXAMPLE 13

In Vivo Potential for Human Cancer Cells

The present invention has potential for use as therapeutic agents. In vivo studies of tumor growth and metastasis of human tumor cells either ectopically or orthotopically transplanted into immune compromised animals, such as nude mice, or in vivo studies employing well recognized animal models are conducted. Inhibition of growth of human tumor cells transplanted into immune compromised mice provide pre-clinical data for clinical trials. In vivo studies include two human tumor cell models, the metastatic non-estrogen responsive MDA-MB-435 breast cancer model, and the androgen non-responsive PC-3 prostate cancer model.

MDA-MB-435 Breast Cancer Model

Pathogen free MDA-MB-435 human breast cancer cells stably transfected with a marker protein (fluorescent green protein) are grown as a solid tumor in immune compromised nude or SCID mice. The tumors are removed, and 1 mm sections of equal size are orthotopically transplanted into the mammary fat pad or ectopically transplanted into the hind flank of female nude mice. Tumor growth, metastasis, and death of the animals are determined. Tumor growth is measured by caliper evaluations of tumor size. At the time of sacrifice, tumors are removed, measured for size, and used for histochemical examination. Organs such as spleen, lymph nodes, lungs, and bone marrow, are examined for metastatic MDA-MB-435 cells by histochemical staining of tissue sections for expression of the marker fluorescent green protein.

PC-3 Prostate Cancer Model

Pathogen free PC-3 human prostate cancer cells stably transfected with a marker protein (fluorescent green protein) are grown as a solid tumor in nude mice. The tumors are removed, and 1 mm sections of equal size are ectopically transplanted into the hind flank of male nude mice. Tumor growth, metastasis, and death of the animals are determined. At the time of sacrifice, tumors are removed, measured for size, and used for histochemical examination. Organs such as spleen, lymph nodes, lungs, bone marrow, are examined for metastatic PC-3 cells by histochemical staining of tissues for expression of the marker fluorescent green protein.

Skin Cancer Animal Model

Skin cancer is induced in SENCAR and SKH-1 hairless mice by ultraviolet irradiation and chemical (DMBA) treatments. In addition, mice specifically expressing the oncogene Her-2/neu in skin basal cells that spontaneously develop skin cancer are used. The compounds disclosed herein are topically applied to the skin daily, before and after skin cancer initiation, and development of skin papilloma formation is assessed. Control mice are treated identically except that they receive vehicle treatments topically applied to their skin. The efficacy of these compounds in treating papilloma's as well as their ability to affect malignant conversion when supplied prior to premalignant progression is monitored.

EXAMPLE 14

Supplementation with Novel Compounds

Prior to initiation of the in vivo experiments, the compounds of this invention that exhibit the greatest amount of tumor cell killing are adminstered to nude, SCID, transgene, and other mice at varing levels to establish the highest level of compound that can be administered safely without adverse effects. The compounds are administered in a model-appropriate manner; e.g., orally, injections, including injections directly into the target organ, or topically. After establishing the highest level of the compounds that can be tolerated and effective administration routes, the novel compounds are administered to the mice on a daily basis, and tumor growth and progression is determined as described above.

EXAMPLE 15

Establishing Maximum Tolerated Dose (MTD)

To establish the maximum tolerated dose (MTD) of compound 1, 25 strain Balb/c mice are placed into the following 5 groups:

Group 1. Non treated

Group 2. Vehicle treated (ETOH+Peanut oil)/0. 1 ml gavage/mouse/day

Group 3. Compound #1 at 20 mgs/0.1 ml gavage/mouse/day

Group 4. Compound #1 at 10 mgs/0.1 ml gavage/mouse/day

Group 5. Compound #1 at 5 mgs/0.1 ml gavage/mouse/day

Compound 1 is dissolved in 100% ethanol and diluted to the appropriate level in vitamin E depleted peanut oil to deliver 20, 10, and 5 mg/0.1 ml volume by gavage. Vehicle control consists of 100% ethanol plus vitamin E depleted peanut oil. Mice are treated daily for 30 days. Whole body weights are taken weekly after initiation of the treatments. There are no differences in the weights of the mice among groups. The mice remain active and show no signs of toxicity.

High performance liquid chromatography (HPLC) analyses are conducted on serum and tissue samples at weekly intervals during the 30 day treatment. Compound 1 is detected in the serum and tissues from all three test groups.

EXAMPLE 16

Preparation of Stock Solution Vehicle and Compound 1 Dilutions

Stock Solution of Compound 1:

Dissolve 2 grams of compound #1 in 5 mls of 100% ethanol (ETOH) and vortex at 37° C.

Compound 1 at 20 mg/0.1 ml gavage/mouse:

Combine 1 ml of compound 1 stock solution, 3 mls of vitamin E depleted peanut oil and 400 mg of compound #1 (dry) and vortex at 37° C.

Compound 1 at 10 mg/0.1 ml gavage/mouse:

Combine 1 ml of compound 1 stock solution and 3 mls of vitamin E depleted peanut oil.

Compound 1 at 5 mg/0.1 ml gavage/mouse:

Combine 0.5 ml of compound 1 stock solution and 3 mls of vitamin E depleted peanut oil.

Vehicle:

Combine 1 ml ETOH 3 mls of vitamin E depleted peanut oil.

EXAMPLE 17

Chemopreventive Properties of Compound 1 in an ACI Rat Cancer Model

Compound 1 is used in vivo to treat transplanted human breast, prostate, and colon tumors transplanted in immune compromised nude mice. The chemopreventive effectiveness of compound 1 in vivo against human breast cancer is shown in an estrogen cancer initiated ACI rat breast cancer model. Approximately 90% of rats implanted with estrogen pellets develop breast cancer within 6 months after estrogen implantation.

Compound 1 is dissolved in 100% ethanol and is diluted to the appropriate dosage using vitamin E depleted peanut oil. The maximum tolerated dose (MTD, maximum dose of compound that can be administered without adverse affects) is determined as described in Examples 14 and 15. Compound 1 is administered at MTD and ½ MTD. ACI rats at 4 weeks of age are subpannicularly implanted with estrogen pellets in the shoulder region. Compound 1 at MTD and ½ MTD is administered by gavage Breast tumors are detected in the control group at approximately 100 days following estrogen implantation. Ninety percent of the control rats develop breast cancer within 6 months after estrogen implantation. Tumor bearing animals from control and treatment groups are sacrificed at various time intervals after treatment initiation, and mammary tissue is examined for obvious tumors, and further examined by histological analyses.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound having a structural formula

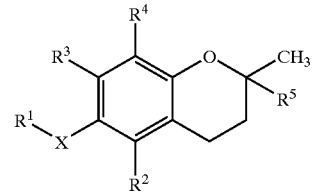

wherein X is oxygen;

wherein $R^1$ is —$C_{1-10}$ alkylene-COOH —$C_{1-4}$ alkylene-CONH2, —$C_{1-4}$ alkylene-COO—$C_{1-4}$ alkyl, —$C_{1-4}$ alkylene-CON($C_{1-4}$ alkylene-COOH)$_2$, $C_{1-4}$ alkylene-OH, $C_{1-4}$ alkylene-NH$_3$-halo, or $C_{1-4}$ alkylene-OSO$_2$NH($C_{1-4}$ alkyl)$_3$;

$R^2$, $R^3$ are H or $C_{1-4}$ alkyl;

$R^4$ is $C_{1-4}$ alkyl; and $R^5$ is $C_{7-16}$ alkyl, COOH, $C_{7-16}$ olefinic group containing 3 to 5 ethylenic bonds, —C=C—COO—$C_{1-4}$ alkyl or $C_{1-4}$ alkylene-COO—$C_{1-4}$ alkyl;

with the proviso that $R^1$ can not be —$C_{2-4}$ alkylene-COOH nor $C_2$ alkylene-OH when $R^2$, $R^3$, $R^4$ are each methyl and $R^5$ is a $C_{16}$ alkyl.

2. The compound of claim 1, wherein said compound is selected from the group consisting of 2,5,7,8-tetramethyl-(2R-(4R, 8R,12-trimethyltridecyl)chroman-6-yloxy)acetic acid, 2,5,7,8-tetramethyl-2R-(4R,8R,12-trimethyltridecyl) chroman-6-yloxy)hexanoic acid, 2,5,7,8-tetramethyl-2R-(4R,8R,12-trimethyltridecyl)chroman-6-yloxy)octanoic acid, 2,5,8-trimethyl-(2R-(4R,8R,12-trimethyltridecyl) chroman-6-yloxy)acetic acid, 2,7,8-trimethyl-(2R-(4R,8R, 12-trimethyltridecyl)chroman-6-yloxy)acetic acid, 2,8-dimethyl-(2R-(4R,8R,12-trimethyltridecyl)chroman-6-yloxy)acetic acid, 2,5,7,8-tetramethyl-2R-(4R,8R,12-trimetbyltridecyl)chroman-6-yloxy)acetamide, methyl 2,5, 7,8-tetramethyl-2R-(4R,8R,12-trimethyltridecyl)chroman-6-yloxy)acetate, 2-(N,N-(carboxymethyl)-2(2,5,7,8-tetramethyl-(2R-(4R8R,12-trimethyltridecyl)chroman-6-yloxy)acetic acid, 2,5,7,8-tetramethyl-(2RS-(4RS,8RS,12-trimethyltridecyl)chroman-6-yloxy)acetic acid, 2,5,7,8-tetramethyl-(2R-(carboxy)chroman-6-yloxy))acetic acid, 2,5,7,8-tetramethyl-2R-(2RS,6RS,10-trimethylundecyl)chrornan-6-yloxy)acetic acid, 2,5,7,8,-tetramethyl-2R-(2,6,10-trimethyl-1,3,5,9E:Zdecatetraen)chroman-6-yloxy)acetic acid, 3-(2,5,7,8-tetramethyl-(2R-(4R,8,12-trimethyltridecyl)chroman-6-yloxy)propyl-1-ammonium chloride, 2,5,7,8,-tetramethyl-(2R-(heptadecyl)chroman-6-yloxy)acetic acid, 2,5,7,8-tetramethyl-(2R-(heptyl)chroman-6-yloxy)acetic acid, 2,5,7,8,-tetramethyl-(2R-(tridecyl)chroman-6-yloxy)acetic acid, 2,5,7,8,-tetramethyl-2R-(4,8,-dimethyl-1,3,7E:Znonotrien)chroman-6-yloxy) acetic acid, EZ,RS,RS-(phytyltrimethylbenzenethiol-6-yloxy)acetic acid, (R)-2((2,5,7,8-tetramethyl-2-(3propenemethylester)chroman-6-yloxy), and 2,5,7,8-tetramethyl-(2R-(propionate)chroman-6-yloxy)acetic acid.

3. A pharmaceutical compound, comprising the compound of claim 1 and a pharmaceutically acceptable carrier.

\* \* \* \* \*

UNITED STATES PATENT AND TRADEMARK OFFICE
CERTIFICATE OF CORRECTION

PATENT NO. : 6,417,223 B1
DATED : July 9, 2002
INVENTOR(S) : Bob G. Sanders et al.

It is certified that error appears in the above-identified patent and that said Letters Patent is hereby corrected as shown below:

Column 2,
Line 17, "E alpha" should read -- E-alpha --.
Line 23, "a has three" should read -- α has three --.

Column 3,
Line 64, please move the period after the word "summarized".

Column 4,
Line 55, "b y" should read -- by --.

Column 5,
Line 31, "growth; i.e." should read -- growth-i.e. --.

Column 7,
Line 10, "is" should read -- are --.

Column 8,
Line 3, please delete the line space before "Reagent employed".
Lines 25 and 64, "Acid" should read -- acid --.
Line 59, "C—O" should read -- C-O --.
Line 63, please insert a line break after "NOSEY".

Column 9,
Lines 23 and 56, "C—O" should read -- C-O --.
Line 25, please insert a line break before "2,5,7,8-Tetramethyl".
Line 27, "Acid" should read -- acid --.

Column 10,
Line 23, "C—O" should read -- C-O --.
Line 25, please insert a line break before "2,5,7,8-Tetramethyl".
Line 27, "Acid" should read -- acid --.

Column 11,
Lines 24 and 52, "C—O" should read -- C-O --.
Line 27, please insert a line break before "2,5,7,8-Tetramethyl".
Lines 28 and 55, "Acid" should read -- acid --.
Line 54, please insert a line break before "2,5,8-Trimethyl".

UNITED STATES PATENT AND TRADEMARK OFFICE
CERTIFICATE OF CORRECTION

PATENT NO. : 6,417,223 B1
DATED : July 9, 2002
INVENTOR(S) : Bob G. Sanders et al.

It is certified that error appears in the above-identified patent and that said Letters Patent is hereby corrected as shown below:

Column 12,
Line 51, "C—O" should read -- C-O --.
Line 53, please insert a line break before "2,7,8-Trimethyl".
Line 55, "Acid" should read -- acid --.

Column 13,
Line 37, "C—O" should read -- C-O --.
Line 39, please insert a line break before "2,8-Dimethy".
Line 40, "Acid" should read -- acid --.

Column 14,
Line 38, "C—O" should read -- C-O --.

Column 15,
Lines 19 and 55, "C—O" should read -- C-O --.
Line 21, please insert a line break before "Methyl2,5,7,".
Line 56, "Acid" should read -- acid --.

Column 16,
Lines 21 and 51, "C—O" should read -- C-O --.
Line 54, please insert a line break before "2-(2,5,7,8-Tetramethyl".

Column 17,
Line 47, "C—O" should read -- C-O --.
Line 48, please insert a line break before "2-(2,5,7,8-Pentamethylchroman".
Line 49, "Acid" should read -- acid --.

Column 18,
Line 27, please insert a line break before "2,5,7,8-Tetramethyl".
Line 28, "Acid" should read -- acid --.
Line 66, "C—O" should read -- C-O --.

Column 19,
Lines 2 and 33, "Acid" should read -- acid --.
Line 32, please insert a line break before "2,5,7,8-Tetramethyl".
Line 61, "7.5ml" should read -- 7.5 ml --.

Column 20,
Line 32, "hr" should read -- h --.
Line 57, "gm" should read -- g --.

UNITED STATES PATENT AND TRADEMARK OFFICE
CERTIFICATE OF CORRECTION

PATENT NO. : 6,417,223 B1
DATED : July 9, 2002
INVENTOR(S) : Bob G. Sanders et al.

It is certified that error appears in the above-identified patent and that said Letters Patent is hereby corrected as shown below:

Column 21,
Line 39, please insert a line break before "2,5,7,8-Tetramethyl".
Line 52, "gms" should read -- g --.
Lines 53 and 54, "gm" should read -- g --.
Line 55, "hr" should read -- h --.
Line 66, please insert a space before "(10 mmol)".

Column 22,
Line 27, "gm" should read -- g --.
Line 53, please delete the word "give".
Line 56, "minutes" should read -- min --.
Lines 60 and 67, please insert a space before "E:Z".
Lines 60 and 67, please insert a space before "decatetraen".

Column 23,
Line 20, please insert a line break before "3-(2,5,7,8-Tetramethyl".
Line 21, "Chloride" should read -- chloride --.

Column 24,
Line 15, "C—O" should read -- C-O --.
Line 46, please insert a line break before "2,5,7,8-Tetramethyl".
Line 47, "Acid" should read -- acid --.

Column 25,
Lines 12 and 41, "C—O" should read -- C-O --.

Column 26,
Lines 12 and 50, "C—O" should read -- C-O --.
Line 17, "Sulfate" should read -- sulfate --.
Line 54, "Acid" should read -- acid --.

Column 27,
Line 3, please delete the words "to a".
Lines 20 and 48, "C—O" should read -- C-O --.
Line 41, "J$_{gem}$" should not be italicized.
Line 42, "J$_{cis}$" should not be italicized.
Line 42, "J$_{trans}$" should not be italicized.
Line 66, "ar—CH$_2$" should read -- ar-CH$_2$ --

UNITED STATES PATENT AND TRADEMARK OFFICE
CERTIFICATE OF CORRECTION

PATENT NO. : 6,417,223 B1
DATED : July 9, 2002
INVENTOR(S) : Bob G. Sanders et al.

It is certified that error appears in the above-identified patent and that said Letters Patent is hereby corrected as shown below:

Column 28,
Lines 5 and 30, "C—O" should read -- C-O --.
Line 32, please insert a line break before "2,5,7,8-Tetramethyl".
Line 33, "Acid" should read -- acid --.

Column 29,
Line 22, please insert a line break before "2,5,7,8-Tetramethyl".
Lines 30 and 45, "Acid" should read -- acid --.

Column 30,
Line 4, please insert a space before "E:Z".
Line 4, please insert a space before "nonotrien".
Lines 5 and 26, "Acid" should read -- acid --.

Column 31,
Line 18, "becomes" should read -- became --.
Line 58, "Ar—H" should read -- Ar-H --.
Line 59, "Ar—S—Ch$_2$" should read -- Ar-S-CH$_2$ --.
Line 60, "Ar—CH$_3$" should read -- Ar-CH$_3$ --.
Line 60, "Ar—CH$_3$" should read -- Ar-CH$_3$ --.
Line 61, "Ar—CH$_3$" should read -- Ar-CH$_3$ --.

Column 32,
Line 21, "Ar—S—CH$_2$" should read -- Ar-S-CH$_2$ --.
Line 22, "Ar—CH$_3$" should read -- Ar-CH$_3$ --.
Line 22, "Ar—CH$_3$" should read -- Ar-CH$_3$ --.
Line 22, "Ar—CH$_3$" should read -- Ar-CH$_3$ --.
Line 25, please insert a line break before "(R)-2".
Line 40, "hr" should read -- h --.

Column 33,
Line 13, please insert a space before "yield".
Line 18, please insert a line break before "2,5,7,8-Tetramethyl".
Line 19, "Acid" should read -- acid --.
Line 30, "3propenemethylester" should read -- 3 propene methylester --.

Column 34,
Line 14, "fifteen" should read -- 15 --.
Lines 14 and 49, "twenty-nine" should read -- 29 --.

UNITED STATES PATENT AND TRADEMARK OFFICE
CERTIFICATE OF CORRECTION

PATENT NO.    : 6,417,223 B1
DATED         : July 9, 2002
INVENTOR(S)   : Bob G. Sanders et al.

It is certified that error appears in the above-identified patent and that said Letters Patent is hereby corrected as shown below:

Column 37,
Lines 41 and 43, "hours" should read -- h --.

Column 38,
Line 27, "hours" should read -- h --.
Line 27, "hours" should read -- h --.
Line 62, "down stream" should read -- downstream --.

Column 39,
Line 53, "hours" should read -- h --.

Column 40,
Line 53, "papilloma's" should read -- papillomas --.

Column 42,
Line 9, please insert a period after "gavage".

Column 44,
Line 4, please insert a space before "E:Z".
Line 4, please insert a space before "nonotrien".

Signed and Sealed this

Fifteenth Day of April, 2003

JAMES E. ROGAN
*Director of the United States Patent and Trademark Office*